United States Patent
Bragagna et al.

(10) Patent No.: US 9,283,037 B2
(45) Date of Patent: Mar. 15, 2016

(54) LASER MICROPORATOR

(75) Inventors: Thomas Bragagna, Feldkirch (AT); Reinhard Braun, Lustenau (AT); Daniel Gfrerer, Bludenz (AT); Bernhard Nussbaumer, Feldkirch (AT); Christof Böhler, Berneck (CH)

(73) Assignee: PANTEC BIOSOLUTIONS AG (LI)

( * ) Notice: Subject to any disclaimer, the term of this patent is extended or adjusted under 35 U.S.C. 154(b) by 2423 days.

(21) Appl. No.: 11/911,850

(22) PCT Filed: Apr. 18, 2006

(86) PCT No.: PCT/EP2006/061639
§ 371 (c)(1),
(2), (4) Date: Oct. 18, 2007

(87) PCT Pub. No.: WO2006/111526
PCT Pub. Date: Oct. 26, 2006

(65) Prior Publication Data
US 2008/0208104 A1 Aug. 28, 2008

(51) Int. Cl.
*A61B 18/20* (2006.01)
*A61B 17/00* (2006.01)
*A61B 18/00* (2006.01)
*A61M 37/00* (2006.01)

(52) U.S. Cl.
CPC ..... *A61B 18/203* (2013.01); *A61B 2017/00765* (2013.01); *A61B 2018/00452* (2013.01); *A61M 37/00* (2013.01); *A61M 2037/0007* (2013.01)

(58) Field of Classification Search
CPC ...................................................... A61B 18/20
See application file for complete search history.

(56) References Cited

U.S. PATENT DOCUMENTS

| | | | |
|---|---|---|---|
| 5,360,447 A * | 11/1994 | Koop | 128/898 |
| 5,554,153 A | 9/1996 | Costello et al. | |
| 5,628,744 A | 5/1997 | Coleman | |
| 5,643,252 A * | 7/1997 | Waner et al. | 606/9 |

(Continued)

FOREIGN PATENT DOCUMENTS

| | | |
|---|---|---|
| EP | 1133953 | 12/2003 |
| GB | 2369057 | 5/2002 |

(Continued)

OTHER PUBLICATIONS

V. Zharov, et al., "Role of photoacoustic effects occurring at lase perforation of skin and laser transcutaneous drug delivery", Proceedings of SPIE—The International Society for Optical Engineering, vol. 3916 (2000), pp. 198-209.

(Continued)

*Primary Examiner* — Lynsey Crandall
(74) *Attorney, Agent, or Firm* — Fish & Tsang LLP

(57) ABSTRACT

The laser micro-porator (10) for porating a biological membrane (1), comprises: a) a laser source (7) that emits a pulsed beam (4), the laser source (7) comprising a laser diode (7c); b) optics (8a,8b,8x) that modify the pulsed beam to direct a laser beam (4) of less that 1 mm width on the biological membrane (1); c) a deflector (8f) oriented to direct the laser beam (4) in various directions; d) a laser beam shaping device that reshapes the energy intensity distribution of the laser beam (4); and e) a poration controller (11) that controls the laser source (7) to create a poration consisting of a plurality of individual pores (2) in the biological membrane (1).

33 Claims, 15 Drawing Sheets

(56) References Cited

U.S. PATENT DOCUMENTS

| | | | |
|---|---|---|---|
| 5,817,089 A * | 10/1998 | Tankovich et al. | 606/9 |
| 5,938,657 A | 8/1999 | Assa | |
| 5,947,956 A | 9/1999 | Karell | |
| 5,947,957 A | 9/1999 | Morris | |
| 5,980,934 A | 11/1999 | Reber | |
| 6,148,232 A | 11/2000 | Avrahami | |
| 6,306,130 B1 | 10/2001 | Anderson | |
| 6,328,733 B1 | 12/2001 | Trost | |
| 6,447,503 B1 | 9/2002 | Wynne et al. | |
| 6,569,157 B1 | 5/2003 | Shain | |
| 2002/0058953 A1 | 5/2002 | Valentin | |
| 2002/0065480 A1 | 5/2002 | Hofmann | |
| 2002/0074320 A1 | 6/2002 | Liu | |
| 2004/0030325 A1 | 2/2004 | Cahir | |
| 2004/0078029 A1 | 4/2004 | Momiuchi et al. | |
| 2004/0220456 A1 | 11/2004 | Eppstein | |
| 2005/0049582 A1 | 3/2005 | DeBenedictis et al. | |
| 2005/0273089 A1 | 12/2005 | Kreindel | |

FOREIGN PATENT DOCUMENTS

| | | |
|---|---|---|
| JP | 8033645 | 2/1996 |
| JP | 2005046247 | 2/2005 |
| WO | WO9409713 | 5/1994 |
| WO | 96/23447 | 8/1996 |
| WO | WO9628212 | 9/1996 |
| WO | 98/29134 | 7/1998 |
| WO | WO9833444 | 8/1998 |
| WO | 9955218 | 11/1999 |
| WO | 0056240 | 9/2000 |
| WO | 00/71045 | 11/2000 |
| WO | 0069515 | 11/2000 |
| WO | 0074767 | 12/2000 |
| WO | 0078242 | 12/2000 |
| WO | 02/089688 | 11/2002 |
| WO | 02092163 | 11/2002 |
| WO | 2003/047449 | 6/2003 |
| WO | 03068197 | 8/2003 |
| WO | WO2004052253 | 6/2004 |
| WO | 2005/092440 | 10/2005 |
| WO | 2006/111199 | 10/2006 |
| WO | 2006/111201 | 10/2006 |
| WO | 2007/39646 | 4/2007 |

OTHER PUBLICATIONS

Woan-Ruoh Lee, et al., "Microdermabrasion as a Novel Tool to Enhance Drug Delivery via the Skin: An Animal Study", Dermatological Surgery, vol. 32 (2006), pp. 1013-1022.

Database CA Chemical Abstracts Service, retrieved from STN Database accession No. 142: 169 416, (2005).

* cited by examiner

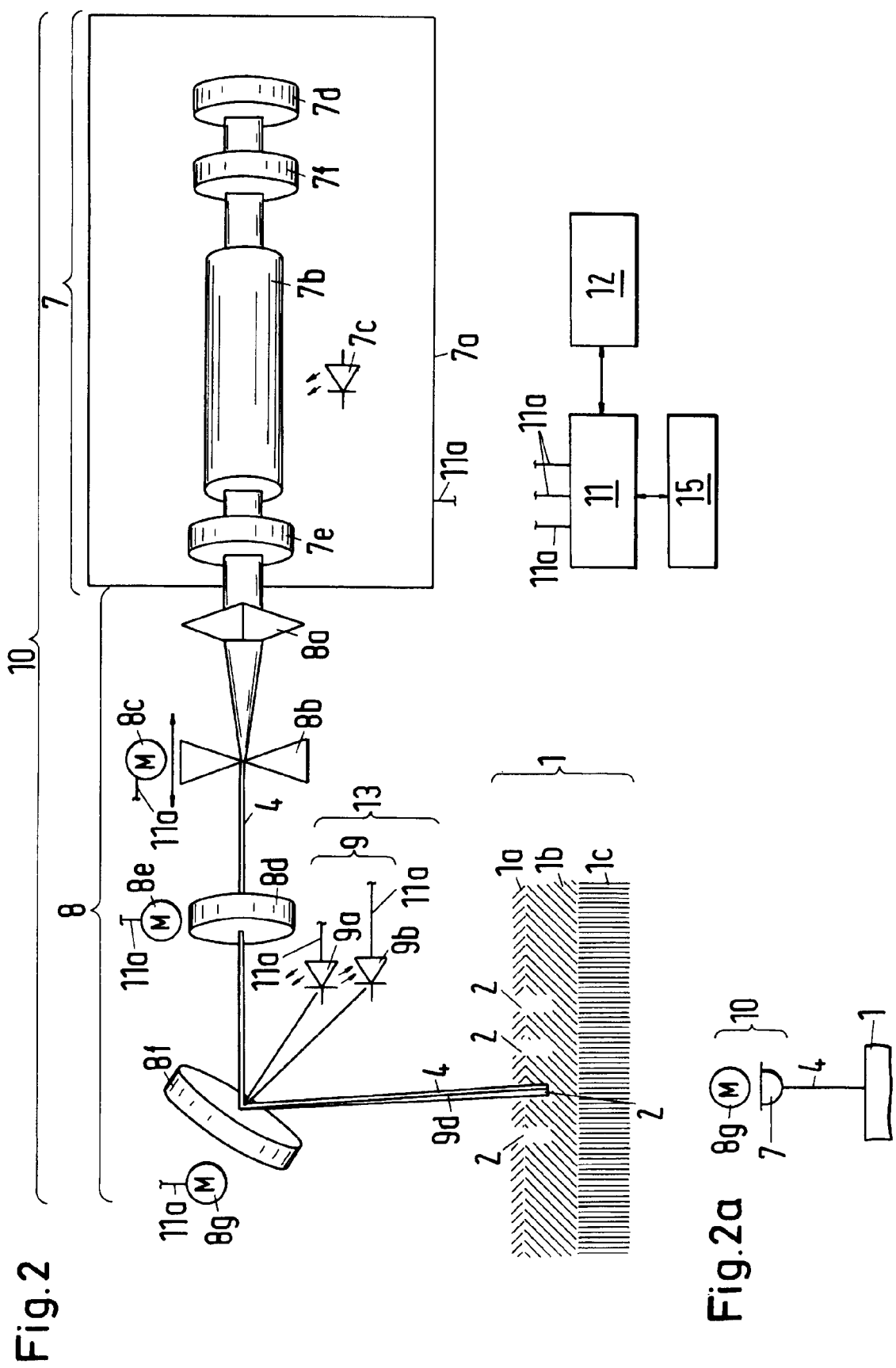

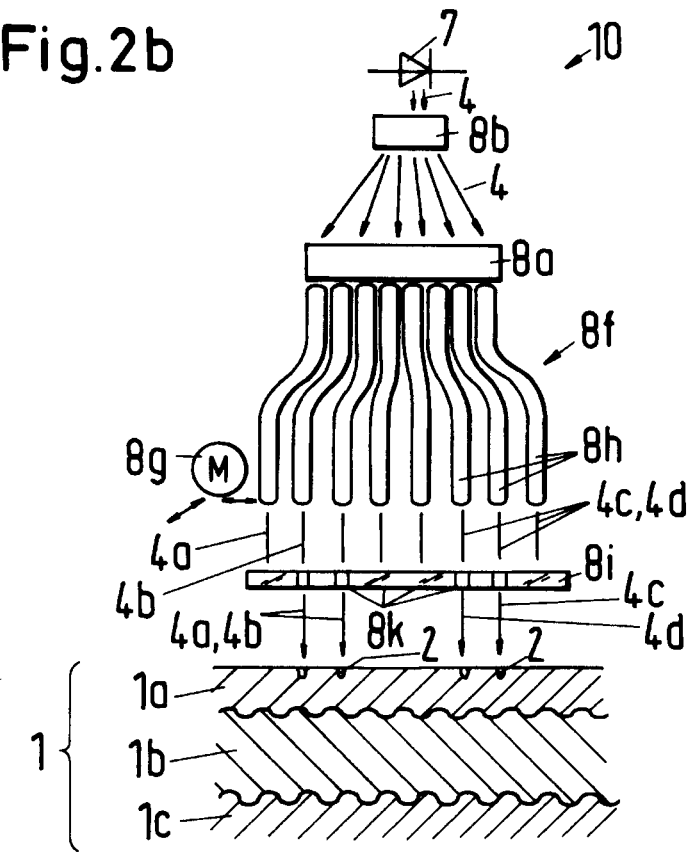
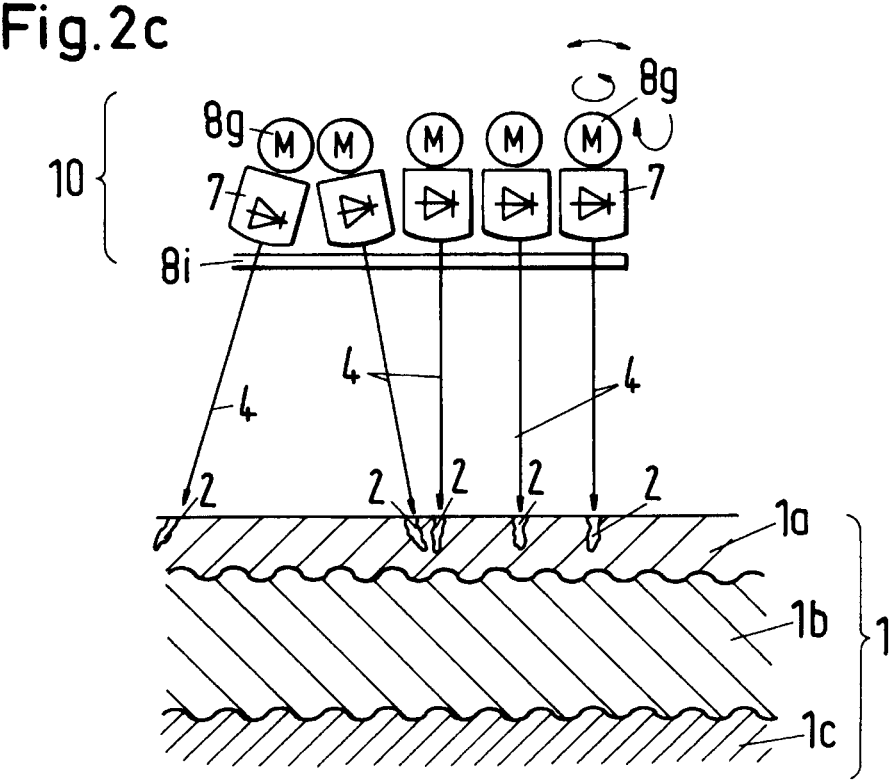

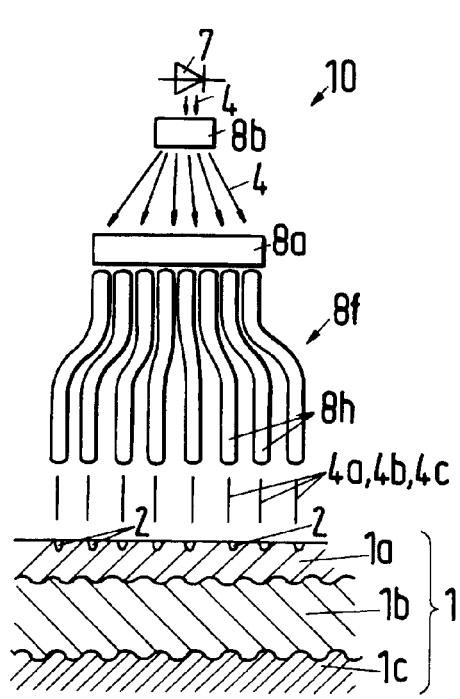
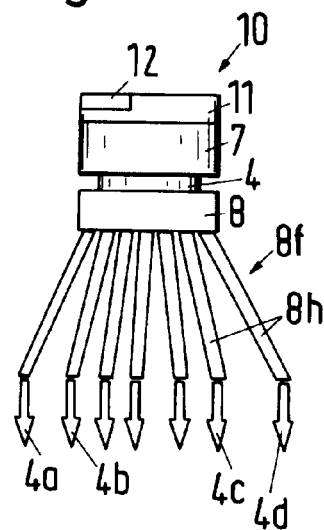
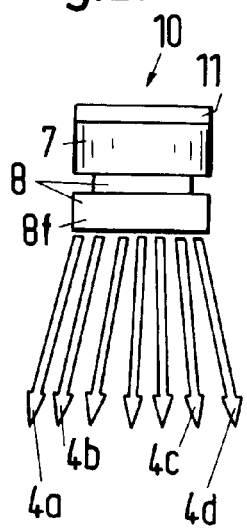
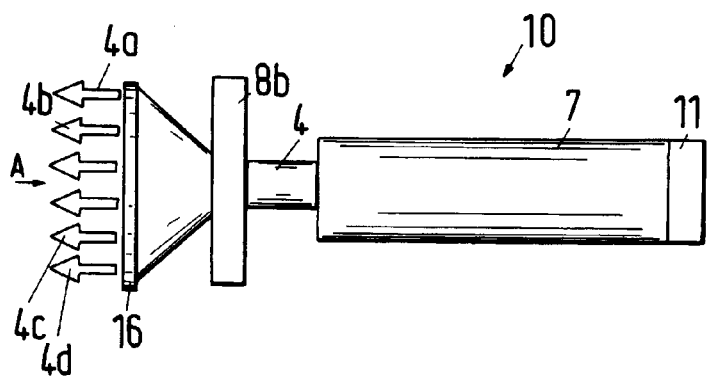
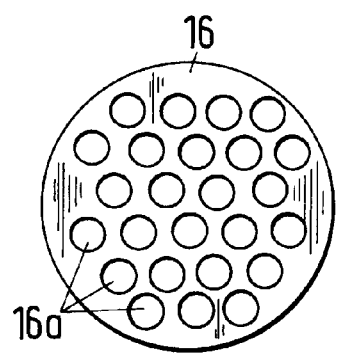

Fig. 2i
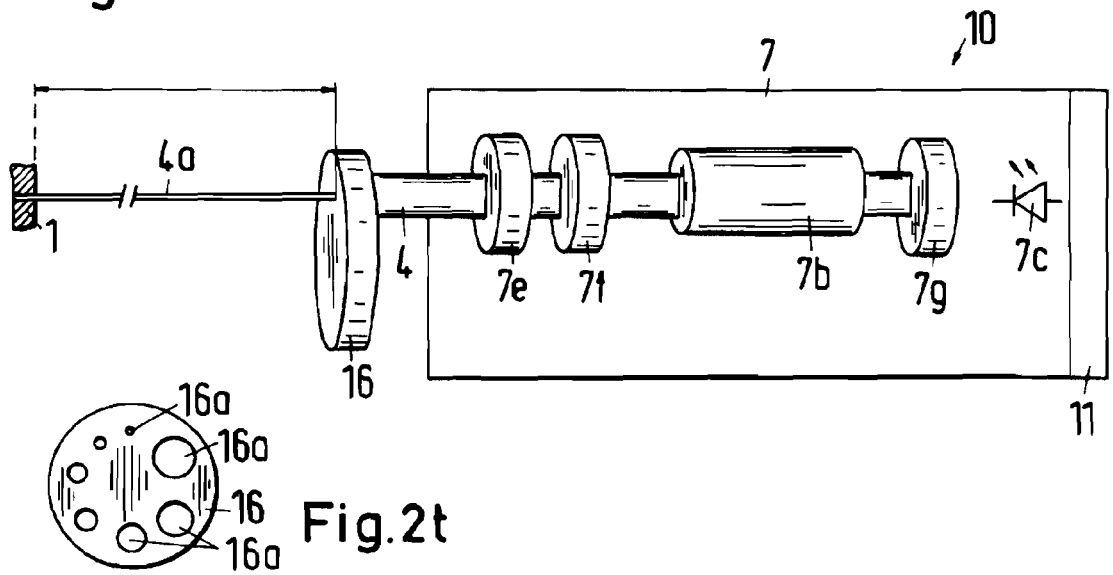
Fig. 2t
Fig. 2k
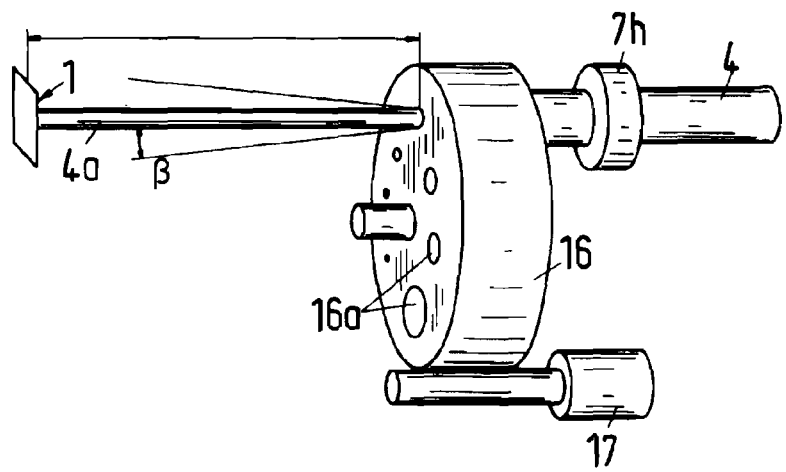
Fig. 2l  Fig. 2m  Fig. 2n
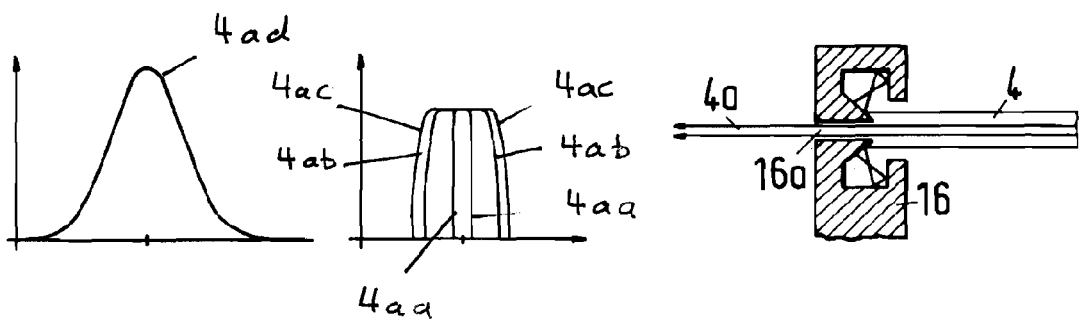

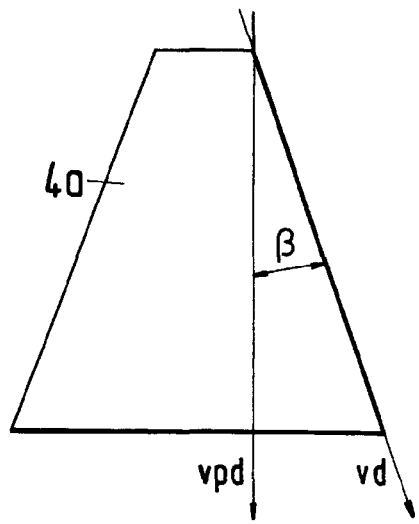
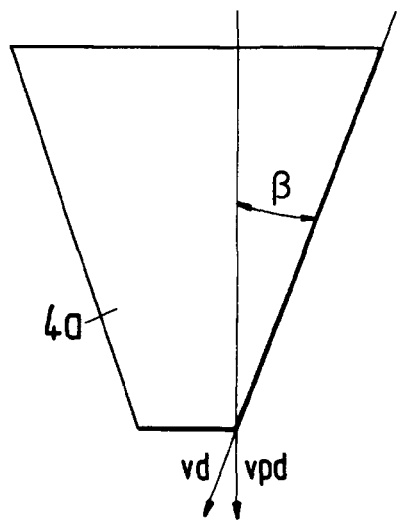
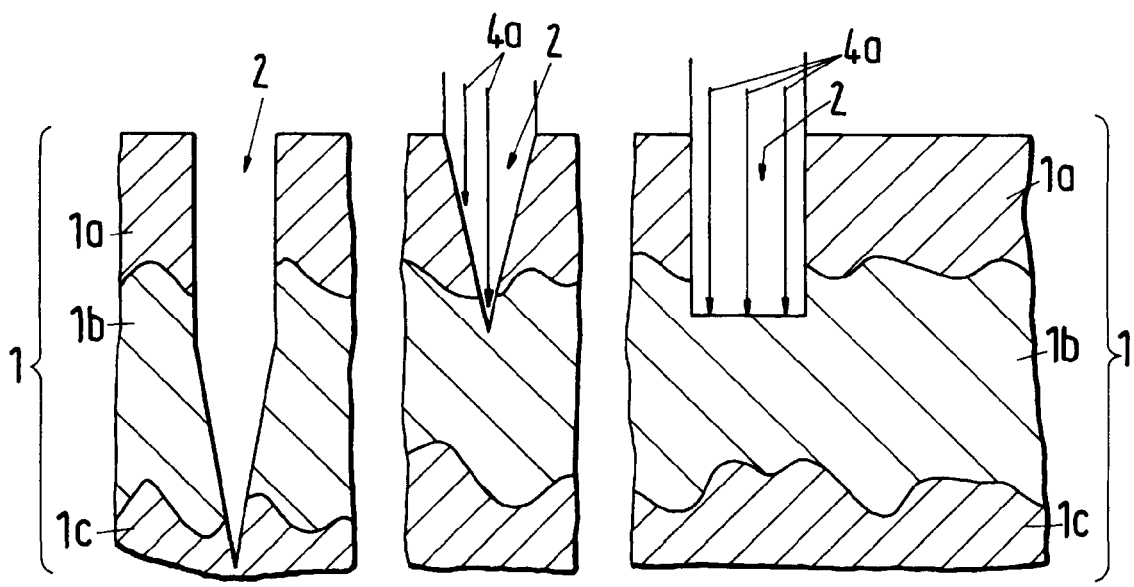

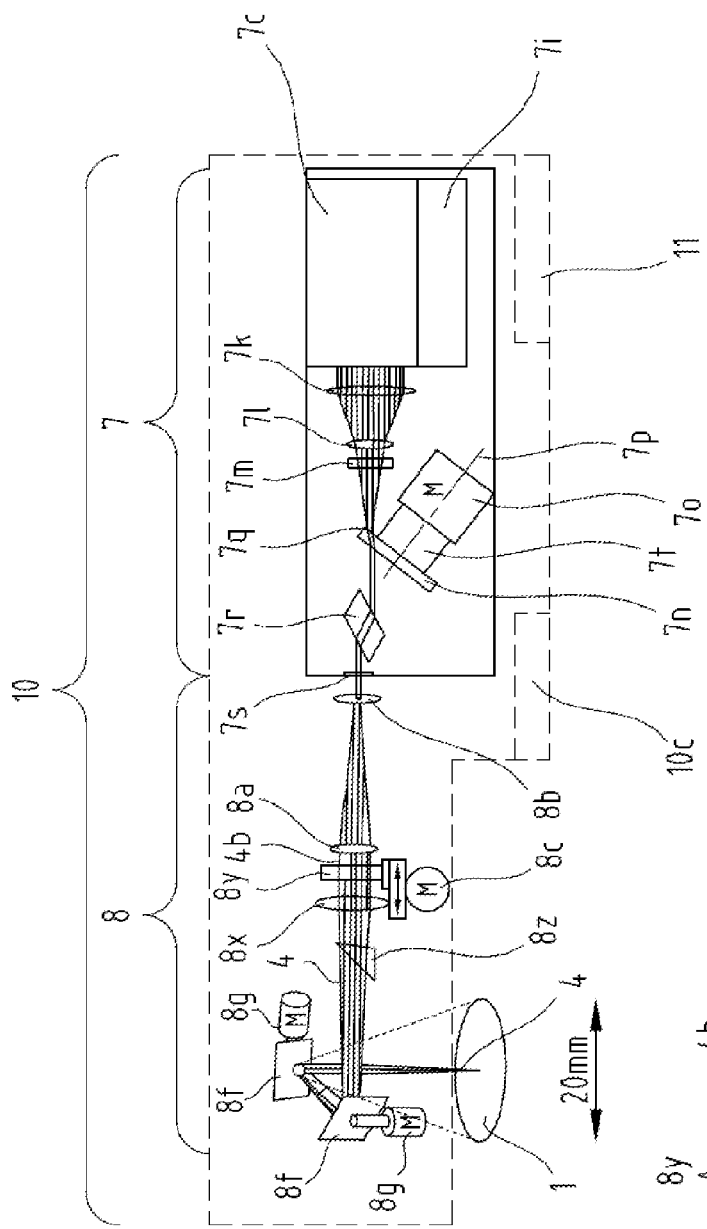
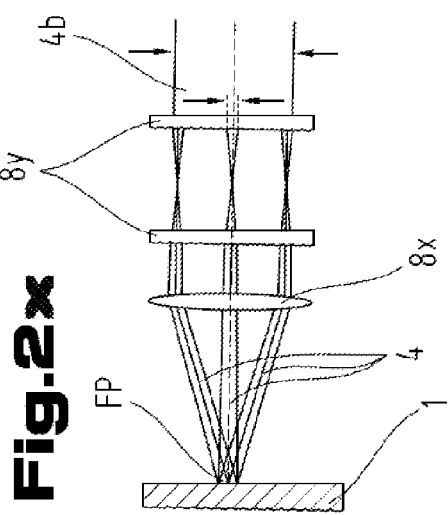

LASER MICROPORATOR

FIELD OF THE INVENTION

This invention relates to a laser microporator and a method for operating the laser microporator for increasing the permeability of biological tissue.

BACKGROUND OF THE INVENTION

Many new and also existing drugs, including vaccines, antigen-presenting cells, therapeutic antibodies, proteins, peptides and DNA constituents, have been developed for better and more efficient treatment for disease and illness. Especially due to recent advances in molecular biology and biotechnology, increasingly potent pharmaceutical agents, such as recombinant human insulin, growth hormone, follicle stimulating hormone, parathyroid hormone, etanercept, and erythropoietin are available. However, one significant limitation in using these new drugs is often a lack of an efficient drug delivery system, especially where the drug needs to be transported across one or more biological barriers at therapeutically effective rates and amounts.

Most drugs are orally administered. However, many drugs, especially protein based drugs (e.g., proteins, peptides, and/or nucleic acids, etc.) cannot be effectively absorbed in this manner due to their degradation in the gastrointestinal tract, poor absorption in intestinal membrane, and/or first pass breakdown by the liver. Thus the bioavailability is very poor, so that very high dose rates have to be applied. To circumvent such difficulties, parenteral administration can be employed. Typically such administration relies on injection of the drug into the patient's circulatory system or muscle tissue or intracutaneous or subcutaneous tissue using standard syringes or catheters. Especially in paediatrics intraosseous applications are used in case of emergency. Unfortunately, needle injection often provokes needle phobia, substantial pain, and/or local damage to the skin in many patients. Moreover, and especially where needle injection-based access to body fluids is required for long-term drug administration, numerous challenges arise. For example, needles tend to clog when left over a prolonged period in a patient's vascular system. Also, mobility of the patient is generally limited. Moreover, needles and catheters might cause infections. Moreover the safe disposal of needles is difficult and expensive, and infection rate by recapping of needles is high.

Alternatively, transmembrane delivery can be employed which usually relies on passive diffusion of a drug across a biological membrane such as the skin. However, transmembrane, in particular transdermal delivery is often not broadly applicable as the skin presents a relatively effective barrier for numerous drugs. The outermost layer of skin, the stratum corneum, is chiefly responsible for the well known barrier properties of skin. Thus, it is this layer that presents the greatest barrier to transdermal flux of drugs or other molecules with a molecular weight of greater than about 500 Dalton into the body. Also the lipophilic or hydrophilic properties, polarity and solubility are important factors for transdermal permeability. Once a drug reaches the dermal region, which is below the epidermal layer, the drug diffuses rapidly to deep tissue layers and other parts of the system via blood circulation. To improve the rate of drug delivery through the skin, chemical enhancers, iontophoresis, electroporation, ultrasound, and heat elements have been used. However, and depending on the particular drug, such techniques frequently fail to provide a therapeutic level of delivery. Worse yet, such techniques will sometimes provoke undesirable skin reactions for long term drug delivery.

Some attempts have been made to improve transdermal delivery using a laser for puncturing the skin of a patient in a manner that does not result in bleeding. Such perforation typically penetrates through the stratum corneum or both the stratum corneum and the epidermis. This allows drug delivery through the skin. An example of such a laser, described in EP 1133953, provides one slit-shaped perforation with a width of up to 0.5 mm and a length of up to 2.5 mm. (This and all other citations herein are incorporated by reference in their entirety). Unfortunately, the rate of drug delivery through such a perforation is limited. This perforation also provokes undesirable skin reactions and the perforation of the skin frequently causes pain. The perforation requires subsequent patch drug application. However, such administration of drugs often results in inconsistent drug dosages, inconvenient usage, and sometimes even in infections.

Document U.S. Pat. No. 6,328,733 discloses a laser porator using a Gaussian laser beam and creating a series of holes or slits onto the scalp for hair transplant. The size and depth of the created holes or slits is relatively large, and they are not suitable for transdermal drug delivery.

Document WO00/78242 discloses a laser porator for forming micropores in the stratum corneum using a Gaussian laser beam. The purpose of this laser porator is to easily gather interstitial fluids for testing analytes present in the fluid. The micropores created with this laser porator are also not suitable for transdermal drug delivery. A further drawback of this laser porator is that if provided with a portable power supply, such as a battery, the total operation time of the laser porator is very short.

Therefore, although there are various methods and devices for drug administration known in the art, all or almost all of them suffer from one or more disadvantages. Among other things, currently known methods and devices fail to allow controlled and reproducible administration of drugs. Currently known methods and devices also fail to provide prompt initiation and cut-off of drug delivery with improved safety, efficiency and convenience. Currently known devices are also limited in forming micropores. Currently known devices are also either not portable or can not be operated during a reasonable time if provided with a portable power supply. It is therefore an object of the present invention to provide devices and methods to improve transmembrane delivery of molecules, including drugs and biological molecules, across biological membranes, such as tissue or cell membranes. This problem is solved with a laser microporator according to the inventive subject matter presented herein.

SUMMARY OF THE INVENTION

The device and method according to the invention utilize a pulsed laser beam and a deflector to direct the laser beam to different locations on a biological membrane, to create a microporation consisting of a plurality of individual micropores or holes. The device comprises a laser beam shaping device which is used to reshape the energy intensity distribution of the laser beam, in particular to get a hard-edged intensity distribution and/or to get a homogenous intensity distribution of the beam, in particular at the focal range, the focal depth, the focal point or the focus on the biological membrane. Such a beam allows creating micropores of very suitable shapes for drug delivery. Such a beam further allows creating micropores with reduced energy, which allows to build a portable microporator, preferably a very small and battery powered microporator. The level of laser energy is within a range that ablates the biological membrane, in particular the stratum corneum and part of the epidermis of the skin. This affects individual micropores in the skin, which results in an increase in skin permeability to various substances. This allows a transdermal or intradermal delivery of substances applied onto the skin. The invention provides a method for enhancing the transmembrane flux rate of a permeant into a selected site of an organism comprising the steps of enhancing the permeability of said selected site of the organism to said permeant by means of porating a biological membrane at said selected site by a laser microporator that forms a plurality of micropores in said biological membrane, thereby reducing the barrier properties of said biological membrane to the flux of said permeant.

As used herein, "poration" "microporation" means the formation of a small hole or pore or a plurality of holes or pores to a desired depth in or through the biological membrane or tissue, such as the skin, the mucous membrane or an organ of a human being or a mammal, or the outer layer of an organism or a plant, to lessen the barrier properties of this biological membrane to the passage of permeants or drugs into the body. The microporation referred to herein shall be no smaller than 1 micron across and at least 1 micron in depth.

As used herein, "micropore", "pore" or "individual pore" means an opening formed by the microporation method.

As used herein "ablation" means the controlled removal of material which may include cells or other components comprising some portion of a biological membrane or tissue caused by any of the following: kinetic energy released when some or all of the vaporizable components of such material have been heated to the point that vaporization occurs and the resulting rapid expansion of volume due to this phase change causes this material, and possibly some adjacent material, to be removed from the ablation site; Thermal or mechanical decomposition of some or all off the tissue at the poration site by creating plasma at the poration site and/or heating via conductive materials.

As used herein, "tissue" means any component of an organism including but not limited to, cells, biological membranes, bone, collagen, fluids and the like comprising some portion of the organism.

As used herein "puncture" or "micro-puncture" means the use of mechanical, hydraulic, sonic, electromagnetic, or thermal means to perforate wholly or partially a biological membrane such as the skin or mucosal layers of a human being, a mammal, a bird or the outer tissue layers of a plant.

To the extent that "ablation" and "puncture" accomplish the same purpose of poration, i.e. the creating of a hole or a pore in the biological membrane optionally without significant damage to the underlying tissues, these terms may be used interchangeably.

As used herein "puncture surface" means the surface of the hole or pore at the outer surface of the biological membrane, which has been ablated or punctured.

As used herein the terms "transdermal" or "percutaneous" or "transmembrane" or "transmucosal" or "transbuccal" or "transtissual" or "intratissual" means passage of a permeant into or through the biological membrane or tissue to deliver permeants intended to affect subcutaneous layers and further tissues such as muscles, bones or other underlying tissues. In the most preferred embodiment the transdermal delivery introduces permeants into the blood, to achieve effective therapeutic blood levels of a drug. In a further preferred embodiment the transdermal delivery of permeants triggers the immune response via the Langerhans cells. The terms mean also the passage of a molecule present in the body ("analyte") out through the biological membrane or tissue so that the analyte molecule can be collected on the outside of the body.

As used herein the term "intradermal" means passage of a permeant into or through the biological membrane or tissue to deliver the permeant to the dermal layer, to therein achieve effective therapeutic or cosmetic tissue levels of a drug, or to store an amount of drug during a certain time in the biological membrane or tissue, for example to treat conditions of the dermal layers beneath the stratum corneum.

As used herein, "permeation surface" means the surface of the tissue surrounding the micropore or pore. "Permeation surface" may mean the surface of an individual micropore or pore, or may mean the total permeation surface, which means the sum of all individual surfaces of all individual micropores or pores.

As used herein, "corrected permeation surface" means the permeation surface corrected by a factor or a specific amount, for example by subtracting the surface of the micropore or pore which is part of the stratum corneum.

As used herein, the term "bioactive agent," "permeant," "drug," or "pharmacologically active agent" or "deliverable substance" or any other similar term means any chemical or biological material or compound suitable for delivery by the methods previously known in the art and/or by the methods taught in the present invention, that induces a desired effect, such as a biological or pharmacological effect, which may include but is not limited to (1) having a prophylactic effect on the organism and preventing an undesired biological effect such as preventing an infection, (2) alleviating a lack or excess of substances (e.g. vitamins, electrolytes, etc.), (3) alleviating a condition caused by a disease, for example, alleviating pain or inflammation caused as a result of disease, (4) either alleviating, reducing, or completely eliminating the disease from the organism, and/or (5) the placement within the viable tissue layers of the organism of a compound or formulation which can react, optionally in a reversible manner, to changes in the concentration of a particular analyte and in so doing cause a detectable shift in this compound or formulation's measurable response to the application of energy to this area which may be electromagnetic, mechanical or acoustic. The effect may be local, such as providing for a local anaesthetic effect, it may be systemic, or it may be not systemic, for example the administration of a radiopaque material, a contrast medium or a liquid to irrigate a tissue. This invention is not only drawn to novel permeants or to new classes of active agents other than by virtue of the microporation technique, although substances not typically being used for transdermal, transmucosal, transmembrane or transbuccal delivery may now be useable. Rather it is directed to the mode of delivery of bioactive agents or permeants that exist in the art or that may later be established as active or passive agents and that are suitable for delivery by the present invention.

Such substances include broad classes of compounds normally delivered into the organism, including through body surfaces and membranes, including skin as well as by injection, including needle, hydraulic, or hypervelocity methods. In general, this includes but is not limited to: therapeutic antibodies, antigen-presenting cells (APC), Polypeptides, including proteins and peptides (e.g., insulin); releasing factors, including follicle stimulating hormone (FSH), Luteinizing Hormone Releasing Hormone (LHRH); carbohydrates (e.g., heparin); nucleic acids; vaccines; and pharmacologically active agents such as antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; parasympathomimetics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough and cold preparations, including decongestants; hormones such as estradiol, testosterone, progesterone and other steroids and derivatives and analogs, including corticosteroids; hypnotics; narcotics; immunosuppressives; muscle relaxants; parasympatholytics; sympatholytics; psychostimulants; sedatives; and tranquilizers, as well as cosmetics and cosmeceuticals. By the method of the present invention, both ionized and nonionized permeants may be delivered, as can permeants of any molecular weight including substances with molecular weights ranging from less than 10 Daltons to greater than 1,000,000 Daltons or nano- or microparticles having weights ranging up to or greater than 1 mg.

As used herein, an "effective" amount of a permeant means a sufficient amount of a compound to provide the desired local or systemic effect and performance at a reasonable benefit/risk ratio attending any treatment. The local effect could also be a sufficient local concentration of a permeant such as a radiopaque material or a contrast medium or a material to test the kidney.

As used herein, "carriers" or "vehicles" refer to carrier materials without significant pharmacological activity at the quantities used that are suitable for administration with other permeants, and include any such materials known in the art, e.g., any liquid, gel, solvent, liquid diluent, solubilizer, microspheres, liposomes, microparticles, lipid complexes, permeation enhancer, or the like, that is sufficiently nontoxic at the quantities employed and does not interact with the drug to be administered in a deleterious manner. Examples of suitable carriers for use herein include water, buffers, mineral oil, silicone, inorganic or organic gels, aqueous emulsions, various alcohols, liquid sugars, cyclodextrins, surfactants, lipids, microparticles and nanoparticles, waxes, petroleum jelly, and a variety of other oils, polymeric materials and liposomes.

As used herein, a "biological membrane" means a tissue material present within a living organism that separates one area of the organism from another and, in many instances, that separates the organism from its outer environment. Skin and mucous and buccal membranes are thus included as well as the outer layers of a plant. Also, the walls of a cell, organ, tooth, bone, or a blood vessel would be included within this definition.

As used herein, "mucous membrane" or "mucosa" refers to the epithelial linings of the mouth, tongue, oropharynx, nasopharynx, larynx, respiratory tract, urogenital tract, gastrointestinal tract, anus, gut, eye, conjunctiva, cornea and all other surfaces accessible via an endoscopic device such as the bladder, colon, lung, blood vessels, heart and the like.

As used herein, the "buccal membrane" includes the mucous membrane of the mouth.

As used herein, "transdermal flux rate" is the rate of passage of any analyte out through the skin of a subject or the rate of passage of any bioactive agent, drug, pharmacologically active agent, dye, particle or pigment in and through the skin separating the organism from its outer environment. "Transmucosal flux rate" and "transbuccal flux rate" refer to such passage through mucosa and buccal membranes and "transmembrane flux rate" refers to such passage through any biological membrane.

The term "individual pore" as used in the context of the present application refers to a micropore or a pore, in general a pathway extending from the biological membrane. The biological membrane for example being the skin, the individual pore then extending from the surface of the skin through all or significant part of the stratum corneum. In the most preferred embodiment the pathway of the individual pore extending through all the stratum corneum and part of the epidermis but not extending into the dermis, so that no bleeding occurs. In the most preferred embodiment the individual pore having a depth between 10 µm (for newborns 5 µm) and 150 µm.

As used herein the term "initial microporation" refers to the total number of pores created. "Initial microporation dataset" refers to the set of data, wherein the initial microporation is defined. The dataset including at least one parameter selected from the group consisting of: cross-section, depth, shape, permeation surface, total number of individual pores, geometrical arrangement of the pores on the biological membrane, minimal distance between the pores and total permeation surface of all individual pores. Preferably the initial microporation dataset defines the shape and geometrical arrangement of all individual pores. Preferably the initial microporation dataset defines the shape and geometrical arrangement of all individual pores, which then will be created using the microporator, so that the thereby created initial microporation is exactly defined and can be reproduced on various locations on the biological membrane, also on different objects, subjects or persons.

As used herein the term "beam shaping device" refers to a device reshaping the energy intensity distribution of the laser beam, so the laser beam preferably becomes a hard-edged and/or a homogeneous intensity distribution.

As used herein the term "homogenous intensity distribution of the beam" refers to a beam or beam spot having homogeneous energy intensity distribution or a uniform cross-sectional energy intensity distribution. Such a beam or beam spot is achieved by using a laser beam shaping device including a beam homogenizer. Such a beam homogenizer may comprise microlenses, preferably a microlens array, for example using refractive, plano-convex microlenses or diffractive optical elements (DOE). The beam homogenizing optic reshapes the output beam from the laser with typically Gaussian intensity distribution into a homogeneous beam having a uniform cross-sectional energy density.

After the perforation a substance such as a drug is applied onto the skin, preferably in form of a transdermal patch. The transdermal patch offers a variety of significant clinical benefits over other dosage forms. Because transdermal drug delivery offers controlled release of the drug into the patient, it enables a defined blood-level profile, resulting in reduced systemic side effects and, sometimes, improved efficacy over other dosage forms. In addition, transdermal patches are user-friendly, convenient, painless, and offer multi-day dosing. Transdermal patches therefore offer improved patient compliance.

The present invention employs a laser to porate the skin of a patient to create individual pores and to create a permeation surface within the biological membrane, e.g. the skin. Poration is produced by irradiating the surface of the target tissue with a pulse or pulses of electromagnetic energy from a laser. Prior to treatment, the wavelength, the energy fluence (energy of the pulse divided by the area irradiated), the pulse temporal width, the irradiation spot size and the geometrical arrangement of individual pores are properly selected to precisely porate the target tissue, to eliminate undesired damage of healthy proximal tissue, and to create a permeation surface of sufficient size. The plurality of laser pulses applied allow creating individual pores having a reproducible shape of the wall surrounding the individual pore and preferably allows also creating a reproducible shape of the lower end of the individual pore. The surface of the wall and the lower end is of importance, in particular the sum of the surface of the wall and the surface of the lower end which are part of the epidermis or the dermis, because this sum of surfaces forms a permeation surface through which most of the permeate passes into the tissue, for example into the epidermis and the dermis. In a preferred embodiment, the laser micro-porator applies a parallel or quasi-parallel laser beam on the biological membrane, which facilitates control over the precise shape of the individual pore. The term "parallel or quasi-parallel laser beam" used herein refers to a laser beam that doesn't focus onto the skin, but that has a divergence of less than 3° to 5° for a minimum of 90% of the beam energy. The laser micro-porator according to the invention, using a parallel or quasi-parallel laser beam, allows creation of individual pores with highly reproducible permeation surfaces. In a further preferred embodiment, the laser micro-porator comprises optics that focuses the laser beam on the biological membrane. In a further embodiment the laser is set to operate in multimode where the beam has multiple Gaussian spots for better energy intensity distribution. In a further preferred embodiment, the laser micro-porator comprises a laser beam shaping device that reshapes the energy intensity distribution of the laser beam to get a homogenous intensity distribution of the beam, in particular a homogenous intensity distribution at the focal range. Suitable beam shaping devices can e.g. be diffractive optical elements (DOE) or refractive beam homogenizers (ROE). Such a beam allows creating micropores of very suitable shapes for drug delivery, in particular micropores with relatively sharp edges. Such a beam also allows to ablate tissue with reduced energy or to save energy, because little or no superfluous tissue is ablated and the created micropores do not have superfluous peaks, but the whole energy of the beam is used to create a suitable shaped micro pore. Several further features may be added to save even more energy, which is necessary to run a portable, and for example battery powered laser micro-porator. Most preferably the pulsed beam having a wavelength between 2.8 microns and 3.1 microns or a wavelength of less than 200 nanometers, because water has a high absorption coefficient within these ranges. Such a beam also allows to run a microporator with little energy or to save energy, because the wavelength is very efficient to in particular ablate human skin and to therefore create a plurality or a large amount of pores with limited energy. Most preferably a Q-switched laser source is used, to create a wavelength between 2.8 and 3.1 microns. Most preferably a high efficient laser diode is used to pump the laser source. Most preferably the diameter of the beam is of less than 1 mm, so the needed energy per pulse is just high enough to stay above the ablation threshold of for example 1 Joule per square cm for human skin. Preferably pulses having a temporal width of less than 1 μs are used, most preferably between 50 ns and 150 ns. Such a temporal width reduces the thermal damage of tissue surrounding a micro pore to a minimum because of the thermal relaxation time of water at wavelengths at 3 microns is about 1 μs. So heat conduction in the skin is very low and only given by very high pulse repetition rates. A temporal width of less than 150 ns further reduces the heating of tissue surrounding a micro pore due to the fact that thermal relaxation is low also at high pulse repetition rates. A further benefit of these short pulse widths is the partial generation of plasma ablation and the generation of cavitation bubbles. These bubbles cause high pressure waves that disorder the intercellular bondings which additionally increases the flux rate of a permeant through a tissue. A further benefit of these short pulse widths is the reduction of the cell sealing mechanism which reduces permeant flux and activation of the Langerhans cells. Free running lasers with pulse widths of more than 50 μs cause a collateral tissue damage like cell sealing in the area adjacent to the pore, the area having a depth of about 15 to 25 microns. Short pulsed lasers with low repetition rates and less than 1 μs pulse width or high repetition rate lasers with pulse widths less than 150 ns cause collateral damage of less than 2 to 4 microns. Thermal relaxation is the process by which heat diffuses through tissue or water by conduction. When the laser exposure is less than the thermal relaxation time there is minimal thermal damage. The thermal relaxation time of skin could be around 1 ms, and the thermal relaxation time of water could be around 1 μs. If laser light of such pulse length or longer would be applied to tissue, a high thermal transfer of heat would occur to the surrounding tissue. Because of the short pulses applied, which in a preferred embodiment are below the thermal relaxation time of skin or water, the tissue is not damaged. Both effects allow to reduce the needed energy per pulse. These measures, alone or in combination with each other, allow to build a laser porator which needs only little energy to create an initial microporation on the biological membrane, the initial microporation preferably comprising between 100 and 10000 individual pores. The pulse repetition frequency of the laser source is preferably higher than 200 Hz, most preferably higher than 1 kHz. This means that the total time to create the entire initial microporation needs preferably less than 10 seconds. The benefit of this short period of time is that the thermal capacity of elements of the laser porator, for example the electronic elements or the housing, can be used to store the heat generated during the formation and creation of the initial microporation. Because the period of time to create the initial microporation is so short, the elements do not overheat and may cool down after the initial microporation is terminated. Therefore in a preferred embodiment the laser porator requires no active cooling means like a ventilator which dissipates further energy. The laser porator comprising the laser source, the optics, the deflector, the laser beam shaping device and the porator controller may be fitted within a housing sized, shaped and of a weight to comfortable fit in the hand of a laser porator user. Most preferably the laser porator comprises also a power supply arranged within the housing. The power supply may consist of a battery, for example a rechargeable or replaceable battery, but may also consist of other types of power supplies such as fuel cells, power capacitors or photovoltaic elements. Depending on the elements combined, the hand held laser porator may create with one single power supply about hundred initial microporations, each microporation for example comprising 100 individual pores. Afterwards the power supply has to be recharged.

In a preferred embodiment, at least two pulses of the laser beam are directed to the same pore. The deflector is built or controlled such that a second, third or even more laser beams are directed into the same pore. This multiple targeting of the same pore also allows using a laser beam of relative low energy. This makes sense because the maximum optical penetration depth is for example about 2 to 4 microns in human skin at wavelengths of about 3 microns. It is therefore very inefficient to create very deep pores of 70 to 200 microns with one single laser pulse. This multiple targeting also supports to save energy and to build a small laser porator, operated with a portable power supply. Such deep pores of 70 to 200 microns are needed for higher permeation rates of e.g. lipophilic and large hydrophilic permeants through the epidermis to the blood vessels in the dermis. The laser beam may be directed up to ten times or even up to fifty times into the same pore, whereby the beam is preferably directed consecutively into the same pore, to thereby "drilling" microholes into the biological membrane. The beam may also be redirected into a single one of a plurality of pores, after impacting at least one of the plurality of other pores.

In a preferred embodiment, the laser porator comprises means that analyses a characteristic, for example the depth of the individual pore. This feedback loop may, for example, be a spectrograph to detect, based on the reflected light or fluorescence of the intact tissue or the evaporated tissue or tissue plume whether the lower end of the individual pore is within the stratum corneum, within the epidermis or within the dermis. In a further embodiment the feedback loop may be an impedance measurement system for detecting and analysing the decrease of the skin impedance which is caused by poration. In a further embodiment the feedback loop may comprise measurement systems like confocal microscopy, laser triangulation, time of flight measurement, interferometers, optical coherence tomography, line projection or a laser scanning device. In a further embodiment the feedback loop may comprise various light sources that illuminate the pores, for example illuminate the pores from outside the pores, and analyse the shadow generated inside the pore. This feedback loop can also be a device for measuring the depth of the individual pore, for example, a device comprising a laser beam that scans the lower end or the whole 3D structure of the individual pore. It is particularly advantageous to analyse a characteristic of the individual pore each time a laser beam has been emitted into the individual pore. This strategy provides continuous information about the actual depth of each of the individual pores. The pore analysis can for example be carried out after each pulse or for example by random sampling at for statistical analysis useful sampling rates to calculate the properties of the adjacent tissue.

In the most preferred embodiment, the feedback loop is operatively coupled to a poration controller that actuates the laser source. The poration controller compares the measured characteristic of an individual pore with a predetermined value and stops emitting further laser pulses on the individual pore if the characteristic of the individual pore corresponds to the preset value. Most preferred the depth of the individual pore is monitored. This allows creation of an individual pore similar to drilling a hole in a material, in that the depth of the hole e.g. the pore is repeatedly measured. The accuracy of the final depth of the individual pore can, for example, be improved if reduced laser energy is applied per pulse, which causes a smaller amount of biological membrane being ablated per pulse. The laser energy can be varied as a function of the depth of the individual pore, to for example apply lower laser energy during the final shots, to create an individual pore with an accurate final depth. This creates an individual pore for which the permeation surface is known to be accurate or quite accurate. Therefore, the total permeation surface of all individual pores can also be determined. Still further, it is possible to know the depth at which the epidermis starts, for example, by using the spectrograph. Therefore the thickness of the stratum corneum can be measured. Taking into account this information, a pore with a corrected permeation surface can be calculated. This corrected permeation surface for example comprising only the permeation surface of the epidermis. This is of importance, because the transdermal flux rate, depending on the drug applied, often depends on the amount of permeation surface which allows a high passage of drugs, for example, into the lower area of the dermis and the blood. Knowing the corrected permeation surface, which means the permeation surface of the epidermis and/or the dermis, allows one to better control or predict the transdermal delivery of drug into the patient, e.g. to better control or predict the release of the drug into the patient. The method according to the inventions therefore allows control or prediction of the transdermal flux rate through the skin or the biological membrane.

In one embodiment statistical data may be used to estimate the depth of a pore. For at least one of laser parameters such as weave length, pulse length, intensity, beam shape or beam diameter the ablation depth per applied laser pulse can be identified, for example by statistical analysis of a plurality of created pores in function of said laser parameters. Based on the laser parameters applied during the formation of pores, the ablated depth per pulse can be calculated, and knowing the number of pulses applied into the same pore, the total depth of the formed pore may be estimated. This method allows, without the need of a feedback loop, to estimate the depth of created pores.

In one embodiment the width of the laser beam and/or the energy density of the laser beam can be modulated, which allows to modulate the width of the individual pore as well as the ablated depth per pulse.

The laser micro-porator preferably uses a laser source optionally selected from the group consisting of Er:YAG, Er/Pr:YAG, pulsed CO2, Ho:YAG, Er:YAP, Er/Cr:YSGG, Ho:YSGG, Er:YSGG, Er:GGSG, Er:YLF, Tm:YAG, CrTmEr:YAG, Ho/Nd:YAG, CTE:YAG, diode lasers, Fibre lasers, OPO and OPA, free electron lasers to either heat the tissue or to create a plasma of the tissue.

The laser micro-porator preferably uses a laser source having a wavelength between 0.05 microns (micrometers) and 15 microns, preferably between 2 and 10 microns, in particular between 2.8 microns and 3.1 microns or 3.15 microns. Most preferred a wavelength of 2.95 microns is used because there is the absorption maximum of water in the mid infrared range.

The laser micro-porator preferably uses an optical apparatus that generates a laser beam having a width between 0.05 and 0.5 mm. In a preferred embodiment the laser beam has a circular, elliptic or rectangular shape, the width of the circular laser beam being the diameter, the width of the rectangular laser beam being one of the lengths of the rectangle or ellipse.

The laser micro-porator preferably uses a laser source having a pulse temporal width which is between 1 ns and 1000 μs, in particular between 1 ns and 1 μs and most preferred between 10 ns and 50 ns or 50 ns and 150 ns.

The laser micro-porator also preferably uses a laser source having an energy density of the laser beam between 1 mJ/cm$^2$ and 100000 J/cm$^2$, in particular between 10 mJ/cm$^2$ and 5 J/cm$^2$.

One advantage of the invention is that the destroyed surface on the biological membrane is small, which causes minor or no damage of free nerve endings. The invention causes no pain, hardly any irreversible damage of the nervous system, and minor long term effects. Because the destroyed surface is small, the damage of melanocytes is negligible. This hardly causes anomalies in pigmentation, which is on the one hand an aesthetic problem and on the other hand melanocytes are an important protective factor to prevent skin cancer caused by UV radiation (sunlight, solaria).

The micro-porator for porating a biological membrane may comprise or being part of an integrated drug administering system, for example, as the system disclosed in PCT patent application No. PCT/EP2005/051702 of the same applicant, filed on Apr. 18, 2005 and entitled "Microporator for porating a biological membrane and integrated permeant administering system". The biological membrane may be porated according to a method, for example, as disclosed in PCT patent application No. PCT/EP2005/051703 of the same applicant, filed on Apr. 18, 2005 and entitled "Method for creating a permeation surface". All citations herein are incorporated by reference in their entirety. The micro-porator for porating a biological membrane may comprise or being part of a system for transmembrane administration of a permeant, for example, as the system disclosed in PCT patent application No. PCT/EP2006/050574 of the same applicant, filed on Jan. 31, 2006 and entitled "A system for transmembrane administration of a permeant and method for administering a permeant".

BRIEF DESCRIPTION OF THE DRAWINGS

The present invention can be better understood and its advantages appreciated by those skilled in the art by referencing to the accompanying drawings, which are incorporated herein by reference. Although the drawings illustrate certain details of certain embodiments, the invention disclosed herein is not limited to only the embodiments so illustrated. Unless otherwise apparent form the context, all ranges include the endpoints thereof.

FIG. 2 shows a laser micro-porator device;

FIG. 2a-2g show further laser micro-porator devices;

FIG. 2h shows in a view of direction A a plate with a plurality of apertures;

FIG. 2i shows a further laser micro-porator device;

FIG. 2k shows a detail of the laser device according to FIG. 2i;

FIG. 2l, 2m show a laser beam profile;

FIG. 2n show a detail of an aperture;

FIG. 2o, 2p show a parallel or quasi-parallel laser beam;

FIG. 2q shows a lateral view of a pore;

FIG. 2r, 2s show a lateral view of further pores;

FIG. 2t shows a front view of the plate disclosed in FIG. 2i;

FIG. 2u shows a further laser micro-porator device;

FIG. 2x shows a beam homogenizer in detail;

DETAILED DESCRIPTION

Figure 1:
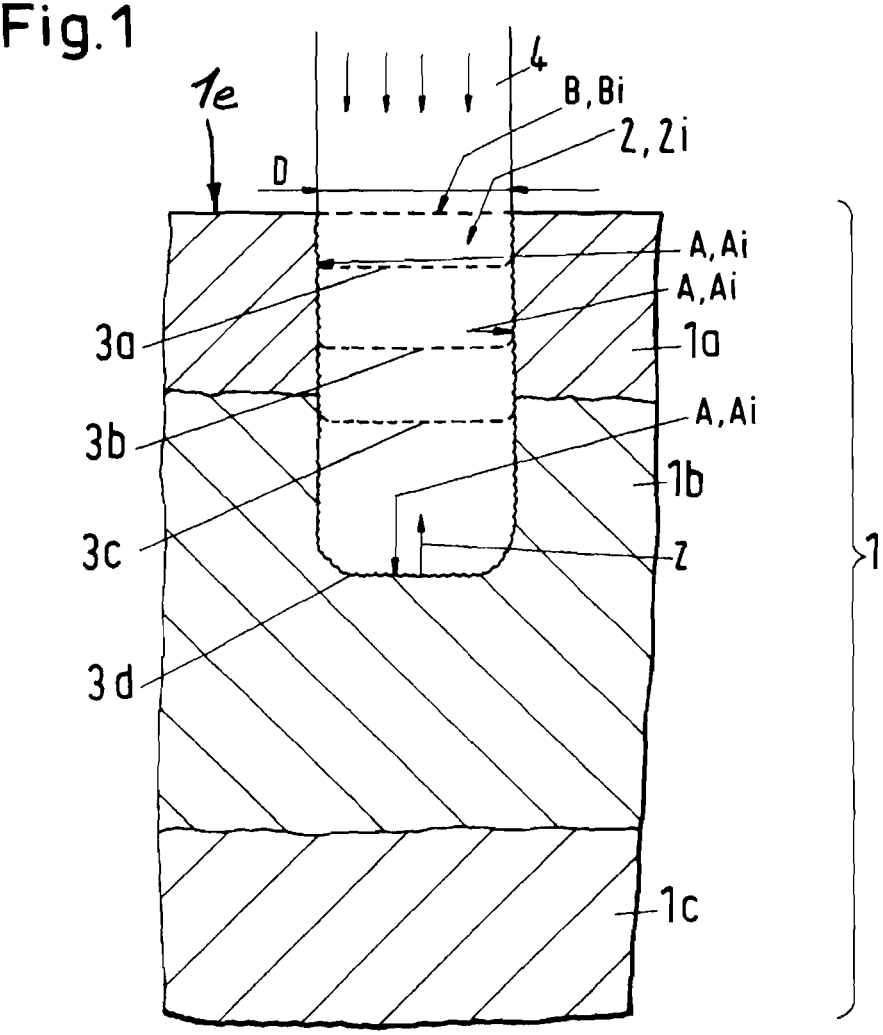
FIG. 1 shows a schematic cross-section of one pore of a laser porated skin.

FIG. 1 shows a cross-sectional view of the top layers of the biological membrane 1, a human skin, having a surface 1e and including a stratum corneum 1a, an epidermal layer or epidermis 1b and a dermal layer or dermis 1c. The outermost layer of skin, the stratum corneum 1a, is a dead cell layer, usually between 10 and 20 microns (μm) thick, but depending on individual differences, the stratum corneum can also have a thickness of only about 5 μm, for example, for a new born child. The stratum corneum 1a contains hydrophilic keratinocytes surrounded by a hydrophobic extra-cellular matrix of lipids, mainly ceramide. Due to the structural and compositional uniqueness, the stratum corneum 1a presents the greatest barrier to transdermal flux of drugs or other molecules into the body, and of body fluids and other analytes out of the body. The stratum corneum 1a is continuously renewed by shedding of corneum cells, with an average turnover time of 2-3 weeks.

Underlying the stratum corneum 1a is the viable epidermis or epidermal layer 1b, which usually is between 50 and 150 μm thick. The epidermis contains free nerve endings but no blood vessels and freely exchanges metabolites by diffusion to and from the dermis 1c, located immediately below the epidermis 1b. The epidermis contains free nerve endings of up to about 1000 per cm². The dermis 1c is between 1 and 3 mm thick and contains blood vessels, lymphatics and nerves. Once a drug reaches the dermal layer, the drug will generally perfuse through system circulation.

FIG. 1 also shows a parallel or quasi-parallel laser beam 4 or a laser beam 4 focused on the skin 1 having a circular shape with a diameter D and acting on the surface of the skin 1. The laser beam 4 may also have other shapes, preferably a rectangular shape. The impact of the laser beam 4 onto the skin 1 causes an ablation of the tissue. A first shot of the laser beam 4 causes an individual pore 2 with a lower end 3a. The first shot effecting a puncture surface B, also called spot B, at the outer surface of the skin 1 in the size of about $(D/2)^2 * \pi$, which corresponds to the amount of the outer surface of the biological membrane, which has been ablated or punctured. A second shot of the laser beam 4 at the same location causes an increase in depth of the individual pore 2 up to the lower end 3b, and a third and forth shot at the same location causes a further increase in depth up to the lower ends 3c and 3d. The total surface of the tissue 1 surrounding the individual pore 2 corresponds to the permeation surface A, which is the sum of the bottom surface and the side wall surface. There is no tissue 1 at the puncture surface B, therefore the puncture surface B is not part of the permeation surface A.

Depending mainly on properties of the tissue, the energy density of the pulsed laser beam 4 and temporal pulse width of the laser beam 4, the increase or decrease in depth per pulse varies. If a focused laser beam 4 is used, the laser beam 4 should preferably have a homogenous intensity distribution within a plane perpendicular to the propagation direction of the beam. The laser beam 4 should preferably at least in the area of the focal depth have a homogenous energy intensity distribution. The use of a laser beam 4 with homogenous intensity distribution or alternatively the use of a non-focused laser beam 4 with a parallel or quasi-parallel laser beam 4 has the advantage, as disclosed in FIG. 1, that the permeation surface A of the individual pore 2 usually has a precise shape, for example a cylindrical shape, and that the bottom of the pore 2 has a precise and preferably flat shape. In the most preferred embodiment, the laser beam 4 is actuated such that the lower end 3c of the individual pore 2 reaches the epidermis 1b but doesn't reach the dermis 1c.

Due to the natural skin renewal process the cells building the epidermis 1b and the stratum corneum 1a grow out of the basal layer. The basal layer is the skin layer between the epidermis 1b and the dermis 1c. Usually 3 to 15 μm a day are renewed. After about 14 days the cells die and build the stratum corneum. After a further period of about 14 days the cells scale off from the skin. So one can say the lower end 3d of each individual pore 2 is moving into the direction of the stratum corneum with a speed of about 3 to 15 μm/day, thereby reducing the permeation surface A. The corrected permeation surface, being the permeation surface of the epidermis 1b only, without the surface of the stratum corneum 1a, becomes the size of the puncture surface, which means the surface of the hole in the stratum corneum 1a, as soon as the cells of the lower end 3d die, due to a genetically programmed cell death, and become the first layer of the stratum corneum 1a. The remaining hole in the stratum corneum 1a will be closed after the already mentioned 14 days. This known mechanism of cell growth and death is not described herein in detail. The constant growing of the cells increases the thickness of the stratum corneum and thus significantly increases the barrier properties in the remaining hole and regenerates the stratum corneum. At the end the individual pore 2 has vanished due to cell growth and the formerly ablated tissue is regenerated by new cells.

Figure 1A:
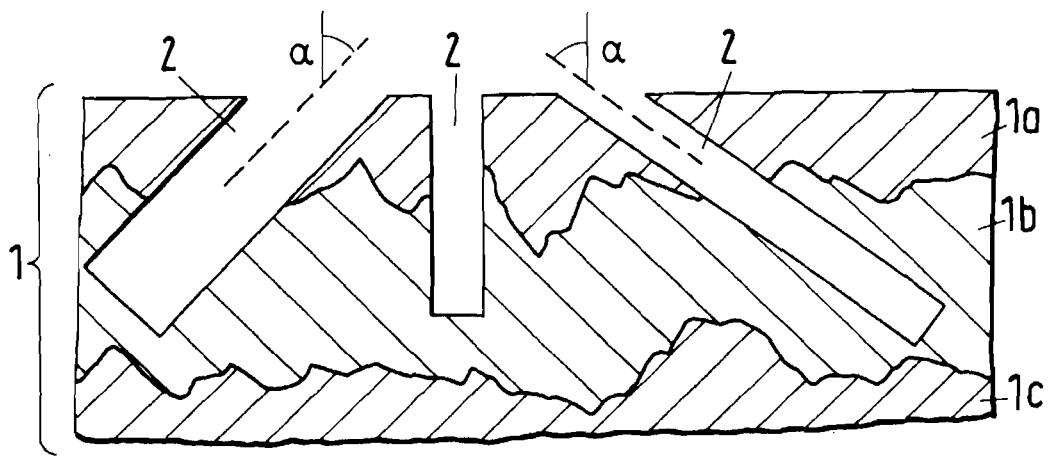
FIG. 1a shows a schematic cross-section of three pores of a laser porated skin

FIG. 1a shows three pores 2. The pore 2 in the middle is perpendicular with respect to the surface of the skin 1, whereas the pores 2 to the left and right penetrate with an angle α into the skin 1, the angle α being in a range between 0° and up to 70°. The advantage of this arrangement of the pore 2 is that the total length of the pore 2 can be very long, without the pore 2 entering into the dermis 1c. The pore 2 to the left or right can for example have double the length of the pore 2 in the middle, including a bigger permeation surface A.

FIG. 2 shows a laser micro-porator 10 comprising a Q-switched laser source 7 and a laser beam shaping and guiding device 8. The laser source 7 has a light source 7c for optical excitation of a laser active material 7b, and a set of reflecting mirrors 7d,7e. The laser source 7 comprises a laser cavity 7a containing a laser crystal 7b, preferably Er and optional additionally Pr doped YAG, which is pumped by an exciter 7c, the exciter 7c being a single emitter laser diode or a set of single emitter laser diode arrays like emitter bars or stacks of emitter bars. The laser source 7 further comprising an optical resonator comprised of a high reflectance mirror 7d positioned posterior to the laser crystal 7b and an output coupling mirror 7e positioned anterior to the laser crystal 7b, and a saturable absorber 7f positioned posterior to the laser crystal. The saturable absorber 7f works as a Q-switch. A focusing lens 8a and a diverging lens 8b are positioned beyond the output coupling mirror 7e, to create a parallel or quasi-parallel laser beam 4 or a focused laser beam 4. Instead of the lenses 8a, 8b, the microporator 10 could comprise different optical means 8a, 8b, which, for example, focus the laser beam 4 onto the surface of the skin 1. The diverging lens 8b can be moved by a motor 8c in the indicated direction. This allows a broadening or narrowing of the laser beam 4, which allows changing the width of the laser beam 4 and the energy fluence of the laser beam 4. A variable absorber 8d, driven by a motor 8e, is positioned beyond the diverging lens 8b, to vary the energy fluence of the laser beam 4. A laser beam shaping device 7h, 8y that reshapes the energy intensity distribution of the laser beam 4 is also included, as disclosed in FIG. 2k or 2u. A deflector 8f, a mirror, driven by an x-y-drive 8g, is positioned beyond the absorber 8d for directing the laser beam 4 in various directions, to create individual pores 2 on the skin 1 on different positions. A control device 11 is connected by wires 11a with the laser source 7, drive elements 8c, 8e, 8g, sensors and other elements not disclosed in detail.

In a preferred embodiment the laser porator 10 also includes a feedback loop 13 respectively a feedback mechanism. In FIG. 2, the feedback loop 13 comprises an apparatus 9 to measure the depth of the individual pore 2, and preferably includes a sender 9a with optics that produce a laser beam 9d, and a receiver with optics 9b. The laser beam 9d has a smaller width than the diameter of the individual pore 2, for example five times smaller, so that the laser beam 9d can reach the lower end of the individual pore 2. The deflection mirror 8f directs the beam of the sender 9a to the individual pore 2 to be measured, and guides the reflected beam 9d back to the receiver 9b. This distance measurement device 9, which can be built in different way, allows measuring the position of the lower end e.g. the depth of the individual pore 2. In a preferred embodiment, the depth of the individual pore 2 is measured each time after a pulsed laser beam 4 has been emitted to the individual pore 2, allowing controlling the effect of each laser pulse onto the depth of the individual pore 2. The feedback loop 13 can be built in various ways to be able to measure a feedback signal of an individual pore 2. The feedback loop 13 may, for example, comprise a sender 9a and a receiver 9b, built as a spectrograph 14, to detect changes in the spectrum of the light reflected by the lower end of the individual pore 2. This allows, for example, detecting whether the actual lower end 3a, 3b, 3c, 3d of the individual pore 2 is part of the stratum corneum 1a or of the epidermis 1b. The laser porator 10 also comprises a poration memory 12 containing specific data of the individual pores 2, in particular the initial microporation dataset. The laser porator 10 preferably creates the individual pores 2 as predescribed in the poration memory 12. The laser porator 10 also comprises one or more input-output device 15 or interfaces 15, to enable data exchange with the porator 10, in particular to enable the transfer of the parameters of the individual pores 2, the initial microporation dataset, into the poration memory 12, or to get data such as the actual depth or the total surface Ai of a specific individual pore 2i. The input-output device 15 can be a card reader, a scanner, a wired interface or for example a wireless connection such as Bluetooth.

The porator further can comprise one or more input-output devices or user interfaces 15 for manually exchange date like data of substances, individuals and much more. The user interface can for example comprise displays, buttons, voice control or a finger print sensor.

There are different ways to build a laser source 7. The laser source 7 may, for example, be built as a laser diode with optics that create a beam 4 of fixed width, for example a width of 250 μm. Laser source 7 can advantageously also comprises an absorber 8d. In a simple version, the laser porator 10 can only comprise the laser source 7 with a built in lens system, and a deflection mirror 8f for direction the laser beam 4 in various directions. Instead of the absorber 8d, the intensity of the laser beam 4 can directly be modulated by driving the laser diode 7 accordingly. As disclosed in FIG. 2a, the position of the laser diode 7 can be modulated by a motor drive 8g, to direct the laser beam 4 on various locations onto the skin 1. Instead of the absorber 8d being arranged after the diverging lens 8b, the absorber 8d can also be arranged within the laser source 7, for example after the output coupling mirror 7e and before the beam 4 leaving the laser source 7.

Instead of the absorber 8d a variable shutter can be used to select a small part of the whole laser beam. To get the preferred homogenous light intensity distribution of the beam, a beam homogenizer such as diffractive optical elements (DOE) (e.g. super gaussian lens or multi level etched wafers) or other optics such as micro-lenses or a micro-lens arrays (MLA) can be positioned between the target tissue and the laser source. The laser source can also be a thin disk laser. The laser diode can also be a laser diode array or a stack of laser diode array that can deliver much more energy than a single laser diode.

The pulse repetition frequency of the laser source 7 is within a range of 1 Hz to 1 MHz, preferably within 100 Hz to 100 kHz, and most preferred within 500 Hz to 10 kHz. Within one application of the laser porator 10, between 2 and 1 million individual pores 2 can be produced in the biological membrane 1, preferably 10 to 10000 individual pores 2, and most preferred 10 to 1000 individual pores 2, each pore 2 having a width in the range between 0.05 mm and 0.5 mm or up to 1 mm, and each pore 2 having a depth in the range between 5 µm and 200 µm, but the lower end of the individual pore 2 being preferably within the epidermis 1b. If necessary the porator 10 is also able to create pores of more than 200 µm depth.

The laser porator 10 also comprises an interlock mechanism, so that a laser pulse is emitted only when it is directed onto the skin 1. The feedback loop 13 could for example be used to detect whether the pulse is directed onto the skin 1. Those skilled in the art will appreciate that there are numerous ways to create an interlock mechanism, and all such ways are contemplated. One embodiment is described in FIG. 4a.

The depth of the individual pore 2 can be measured before and after applying a laser pulse, and due to the fact that the stratum corneum, the epidermis and the dermis have different properties, for example a different amount of water, depending on the change of the amount of the ablation per applied laser pulse, if the same energy per pulse is used, one can determine whether the lower end of the pore is in the stratum corneum, the epidermis or the dermis. In a preferred embodiment, the thickness of the stratum corneum 1a, or if necessary the epidermis 1b can be determined based, on information about the change of the amount of the ablation in depth per pulse. In another embodiment the tissue layers can be differentiated with spectroscopic means.

FIG. 2 discloses a circular laser beam 4 creating a cylindrical individual pore 2. The individual pore 2 can have other shapes, for example in that the laser beam 4 has not a circular but an elliptical shape, a square or a rectangle. The individual pore 2 can also be shaped by an appropriate movement of the deflector 8f, which allows creation of individual pores 2 with a wide variety of shapes.

Figure 3:
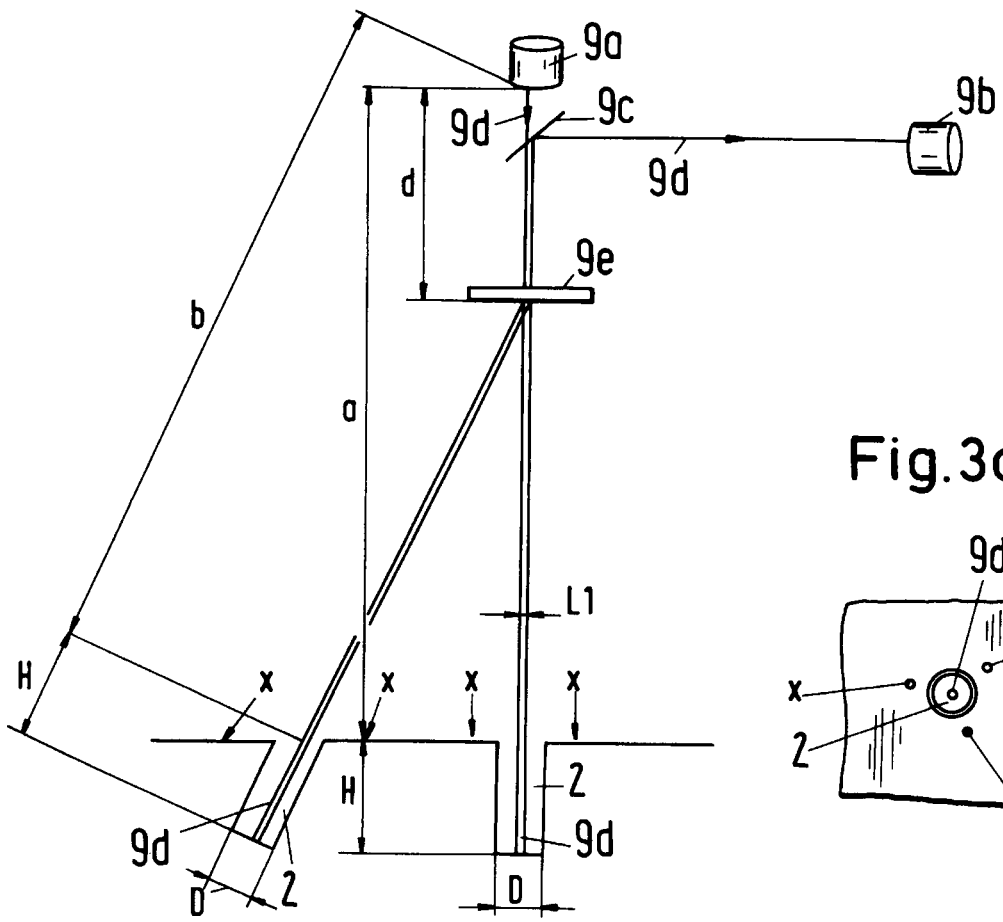
FIG. 3 shows an optional distance measurement device.
Figure 3A:
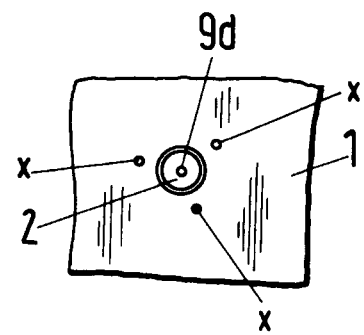
FIG. 3a shows a plan view of the skin, a pore and laser beams of the distance measurement device.

FIG. 3 shows a distance measurement apparatus 9 in detail. The sender 9a emits a laser beam 9d, which passes a semi transparent mirror 9c and a deflector 9e, and gets reflected at the lower end of the individual pore 2, and passes back through the deflector 9e, gets reflected at the semi transparent mirror 9c and enters the receiver 9b. The width L1 of the laser beam 9d is less than the inner diameter D of the individual pore 2, for example five times less. The deflection mirror 9e is able to deflect the laser beam 9d in various directions, and, as disclosed, into various individual pores 2. In a preferred embodiment, the laser beam 9d is also deflected onto the surface of the skin 1, for example on three positions X, the mean value of which defines a reference value. Based on this reference value, the depth H of each individual pore 2 can be measured very accurately, for example with a resolution of 0.5 µm. In one preferred embodiment phase shift technology is used to accurately measure the distance a,b,H between the sender 9a and the point to measure the distance from.

In a further embodiment the distance measurement apparatus 9 is not only able to measure the depth of the individual pore 2, but to measure further characteristics of the individual pore 2, in particular the apparatus can scan the geometrical shape of the whole individual pore 2. This can for example be achieved by an appropriate deflection of the laser beam 9d, using the deflector 9e. Therefore the shape of the side walls of the whole pore 2, which means the shape and also the size of the permeation surface A, can be measured accurately. This arrangement allows a survey of the shape of one or more individual pores 2 in detail. The individual pore 2 may extend perpendicular to the surface of the skin 1, as disclosed on the right side of FIG. 3. The individual pore 2 may also extend oblique with respect to the surface of the skin, as disclosed on the left side of FIG. 3.

In a preferred embodiment the feedback loop 9, 13 is operatively coupled to the poration controller 11, which, for example, can compare the depth of the individual pore 2 with a predetermined value, so that no further pulse of the laser beam 4 is directed to the individual pore 2 if the characteristic of the individual pore 2, for example, the depth, is greater than or equal to a preset value. This allows creation of individual pores 2 with a predetermined depth.

Figure 3B:
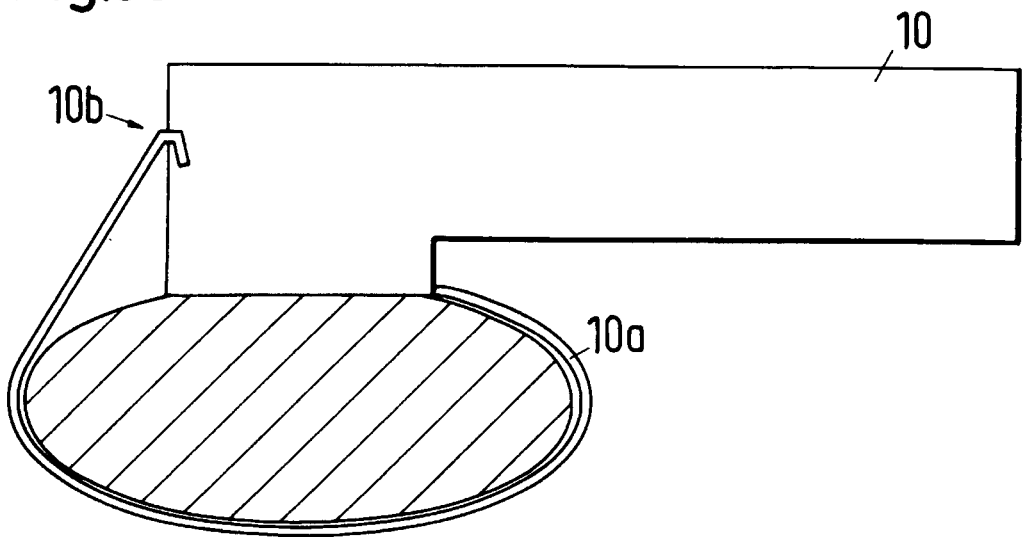
FIG. 3b shows a cross-section of the forearm and a laser micro-porator device on it.

FIG. 3b shows a cross-section of a forearm. A laser microporator device 10 is releasable attached to the forearm using an elastic belt 10a comprising a connector 10b. This attachment allows suppressing or reducing a relative movement between the micro-porator 10 and the area of the forearm on which the front part of the micro-porator 10 is arranged.

The micro-porator 10 preferably needs a time range between less than 1 second and about 10 seconds to create all individual pores 2, depending on the total number of pores 2. It therefore can be advantageous to connect the micro-porator 10 with the body, as disclosed in FIG. 3b, to prevent a relative movement between the micro-porator 10 and the skin 1 during applying the laser beam 4. Usually this connection is not needed, because the total time of the laser beam 4 to create all individual pores 2 is less than 1 second. The chance that a relative movement between the micro-porator 10 and the skin 1 might occur during this period of time is quite small. If a relative movement should occur, which might be detected by the feedback loop 9, the feedback loop 9 can be used to scan the position of the created pores 2 in the skin 1, and based on the thereby known position of the created pores 2, create the remaining pores 2. Therefore, an accurate pattern of pores 2 can be created, even if a relative movement between the micro-porator 10 and the skin 1 occurs during porating.

FIG. 2b shows a further embodiment of a laser microporator 10 comprising a single laser source 7, preferably a laser diode, and a laser beam shaping and guiding device also comprising optical lenses 8b,8a which guide the laser beam 4 into a plurality of fiberoptics 8h, thereby splitting up the laser beam 4 into a plurality of individual laser beams 4a, 4b, 4c, 4d. The laser beam shaping device that reshapes the energy intensity distribution is not disclosed in detail. All fiberoptics 8h together form a deflector 8f, which directs the individual laser beams 4a, 4b, 4c, 4d in various directions. An individual beam 4a, 4b, 4c, 4d is leaving each fiberoptic 8h. The end of the fiberoptic 8h can be moved by a drive 8g, thereby moving the individual beams 4. The fiberoptic 8h is pointing onto the skin 1 to create an individual pore 2 therein. A protective glass 8i can be arranged between the fiberoptic 8h and the surface of the skin 1. The protective glass 8i can further comprise optical switches 8k which allow individually stop, attenuate or let pass the individual laser beams 4a-4d.

FIG. 2c shows a further embodiment of a laser microporator 10 comprising a plurality of individual laser sources 7, preferably laser diodes, each individually driven by a motor 8g, so that the beam 4 of each laser source 7 can individually be directed onto the surface of the skin to create a plurality of individual pores 2. The beam shaping device of the laser sources 7 are not disclosed in detail.

FIG. 2d shows a further embodiment of a laser microporator 10 comprising a single laser source 7, preferably a laser diode, and optical lenses 8b, 8a which guide the laser beam 4 into a plurality of fiberoptics 8h, thereby splitting up the laser beam 4 into a plurality of individual laser beams 4a, 4b, 4c, 4d. All fiberoptics 8h together form a deflector 8f, which directs the individual laser beams 4a, 4b, 4c, 4d in various directions. In contrast to the embodiment according to FIG. 2b the laser micro-porator 10 doesn't comprise a motor 8g and a protective glass 8i. The arrangement of the micropores 2 on the skin 1 is predetermined by the deflector 8f. This laser micro-porator 10 can be built without any moving parts, which allows building a very robust and also very cheap micro-porator 10. This laser micro-porator 10 may for example be only used once, which means a single use laser micro-porator 10. In a further embodiment the fiberoptics is somewhat flexible, so that the final arrangement of the micropores on the skin 1 can be varied by changing the direction of the individual fiberoptics 8h.

FIG. 2e shows a further embodiment of a laser microporator 10 comprising a single laser source 7 and optics 8 which guide the laser beam 4 into a plurality of fiberoptics 8h, thereby splitting up the laser beam 4 into a plurality of individual laser beams 4a, 4b, 4c, 4d. All fiberoptics 8h together form a deflector 8f, which directs the individual laser beams 4a, 4b, 4c, 4d in various directions. The exit end of each fiberoptics 8h has an individually oriented surface, such that the individual laser beams 4a, 4b, 4c, 4d leaving the fiberoptics 8h form an array of, for example, parallel individual laser beams 4a, 4b, 4c, 4d.

FIG. 2f shows a further embodiment of a laser microporator 10 comprising a single laser source 7, optics 8 and a deflector 8f, which split the laser beam 4 into a plurality of individual laser beams 4a, 4b, 4c, 4d, directing in various directions. The optics 8 comprises, for example, an array of micro lenses, which form a deflector 8f. This micro-porator 10 can be manufactured very cheap and is suitable for single use.

FIG. 2g shows a further embodiment of a laser microporator 10 comprising a laser source 7, optics 8 to widen the beam 4, and a hole orifice plate 16 with a plurality of apertures 16a, to form a plurality of individual laser beams 4a, 4b, 4c, 4d. The individual laser beams 4a, 4b, 4c, 4d can be parallel or directing in different directions. FIG. 2h discloses a front view of the hole orifice plate 16 in direction A, as disclosed in FIG. 2g, comprising a plurality of apertures 16a, each aperture 16a generating an individual laser beam 4a.

The laser source 7 disclosed in FIGS. 2b to 2h may be a laser source 7 as for example disclosed in FIG. 2 or a laser diode with collimating optics. FIG. 2i shows a further embodiment of a laser micro-porator 10 with a Q-switched laser source 7 comprising a laser crystal 7b, an exciter or pumping laser diode 7c, and an input coupling mirror 7g, which is a dichroic mirror, an output coupling mirror 7e and a saturable absorber 7f, to create a laser beam 4. The saturable absorber 7f works as a Q-switch. Further Q-switches such as electro optical crystals, acustooptical crystals or rotating Q-switches may be used. The laser-porator 10 further comprises a hole orifice plate 16 with seven apertures 16a of different diameter, in the range of 0.05 to 0.5 mm. FIG. 2t shows a front view of the hole orifice plate 16. In each hole 16a an optional optics may be arranged. The diameter of the beam 4, being emitted to the surface of the skin 1, depends on the diameter of the respective aperture 16a being arranged in the pathway of the beam 4. The hole orifice plate 16 can be rotated, so that the diameter of the emitted beam 4a may be determined by positioning the aperture 16a with the appropriate diameter in the pathway of the beam 4. In a preferred embodiment the distance between the aperture 16a and the skin 1 is in the range of 50 to 60 mm.

FIG. 2k shows the hole orifice plate 16, also called revolver, enlarged. The revolver 16 comprises five to ten apertures 16a of different diameter. A motor 17 drives the revolver to place the appropriate aperture 16a in the pathway of the beam 4, so that the diameter of the beam 4a can be chosen.

FIG. 2l shows a graphical representation of a laser beam intensity profile 4ad of the beam 4 leaving the laser source 7. The intensity profile has a Gaussian distribution. The vertical axis shows the normalized intensity of the laser and the horizontal axis indicates location in the beam 4 with respect to the axial optical centre of the beam 4. In one preferred embodiment, the beam shaping device 8y that reshapes the energy intensity distribution of the laser beam is a homogenizer 7h, 8y that modifies the energy distribution of the laser beam 4 to get a homogenous intensity or energy distribution of the beam 4 may be a super Gaussian lens 7h that is positioned in the pathway of the beam 4, which causes an about rectangular energy intensity profile of the beam 4a. The beam shaping device 7h, 8y may comprise one or two microlens arrays, for example using refractive, plano-convex microlenses. For example a so called "imaging homogenizer" usually consists of two similar microlens arrays with identical lens pitch. The first microlens array is used to divide the incident beam into multiple beamlets. The second microlens array in combination with a behind positioned spherical lens, acts as an array of objective lenses that superimposes the images of each of the beamlets in the first array onto a homogenization plane. The homogenization plane, which is located at one focal length distance behind the spherical lens, is a beam spot having homogeneous energy distribution. FIG. 2m discloses three beam spots having such rectangular energy intensity profiles of three beams 4aa, 4ab, 4ac with different diameter. All three beans 4aa, 4ab, 4ac therefore have so called hard-edged intensity distribution. Such a profile is also called a top hat profile or a flat-top profile. Sharper edges and smaller variations of the flat-top profile of the beams 4aa, 4ab, 4ac may for example be achieved by higher Fresnel numbers due to Fresnel diffraction at the microlens arrays. FIG. 2m discloses that the laser beam 4a has an about constant energy density at the flat-top with respect to the axial optical centre of the beam. Usually, imaging homogenizers consist of two similar microlens arrays with identical lens pitch. Square-type lens apertures generate a square flat top or top hat intensity distribution in the Fourier plane. Other shapes, such as circular or hexagonal microlenses will generate a circular respectively hexagonal flat-top. Also imaging homogenizers consisting of two different microlens arrays may be used, creating various shapes intensity distributions, such as a rectangular or line shape flat-top. The intensity distribution varies in the flat-top with preferably less than 10%.

FIG. 2n shows a cross section of the revolver 16, with an aperture 16a smaller than the laser beam 4, so that the passing laser beam 4a has a reduced diameter. Because the laser beam 4 has an about constant energy density, the energy density of a laser beam 4a passing the aperture 16a is about the same, independent of the diameter of the laser beam 4a.

FIGS. 2o and 2p disclose a laser beam 4a, herein referred to as a parallel or quasi-parallel laser beam. The laser beam 4a has a propagation direction vector vpd of the laser beam 4a and a divergence vector vd of the main divergence of the laser beam 4a. The angle β between the direction vector vpd and the divergence vector vd is less than 3° to 5°, preferably less than 1° and most preferred less than 0.5°. This means the parallel or quasi-parallel laser beam 4a has a divergence of less than 3° to 5°. The diameter of the parallel or quasi-parallel laser beam 4a can become wider as it propagates in vector direction vpd, as disclosed in FIG. 2o, or can become narrower, as disclosed in FIG. 2p. The parallel or quasi-parallel laser beam 4a shows the properties disclosed in FIGS. 2o and 2p at least within a certain range of focus, the focus or focus range, extending in direction of the propagation direction vector vpd, is a range of about 1 cm to 5 cm, preferably a range of 2 cm to 3 cm.

FIG. 2q shows a schematic representation of the lateral view of a pore 2 produced in the skin 1 by the laser beam 4a. The laser beam 4a having a homogeneous energy density, which can be reached by the use of optics, e.g. Gaussian lens, or by a multimode laser beam generation. The laser beam 4a has a so called top hat profile. The laser beam 4a is almost homogeneous with respect to divergence and energy distribution. This laser beam 4a therefore causes a defined ablation of the skin 1 regarding depth and shape. In contrast a laser beam 4 without a homogeneous energy density and/or a laser without a parallel or quasi-parallel laser beam 4 may cause a pore 2 in the skin 1 as disclosed in FIGS. 2r and 2s. The commonly used laser beam 4 has a Gaussian intensity profile as disclosed in FIG. 2l. Such a beam 4 creates pores 2 as disclosed in FIGS. 2r and 2s, comprising a very deep part in the middle. Such a laser beam 4 is very suitable for a laser porator as disclosed in document WO00/78242, because the purpose of this laser porator is to easily gather interstitial fluids. Therefore the most important aspect is that the pore is deep, with a peak in the middle, as disclosed in FIGS. 2r and 2s, whereas the shape of the created pore 2 is of no importance. Such a laser beam 4 may create pores 2 which damage the sensitive layer between the epidermis and the dermis, so that bleeding and pain occurs. Such pores 2 are of no value for transdermal drug delivery. The laser beam 4a as disclosed in FIG. 2q has the advantage that the shape of the pore 2 from top to bottom is kept the same or similar, so that preferably a very exact and reproducible pore 2 is generated. The laser beam 4a of FIG. 2q also allows saving energy, because the created pores 2 do not have peaks in the middle, but the whole energy of the beam is used to create a suitably shaped micro pore. Therefore much less energy is required to create the initial microporation, which allows to use a laser pulse of lower energy, and which allows to use a portable power supply such as battery to drive the laser porator, and to build a hand held laser porator.

Figure 10A:
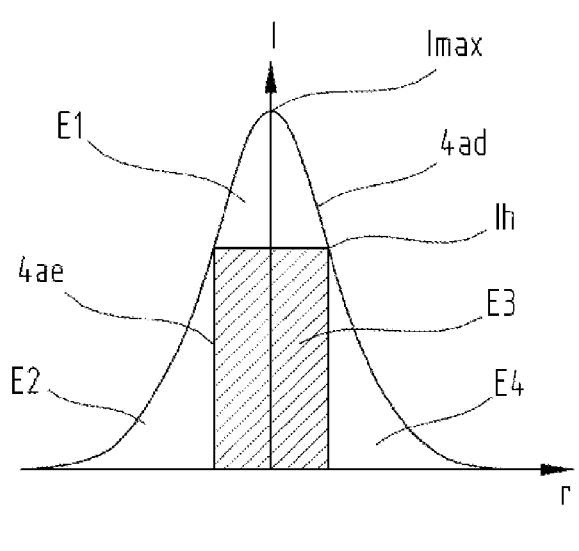
FIG. 10a shows schematically the intensity distribution of a beam without and with beam shaping.

FIG. 10a shows a laser beam 4ad with a Gaussian intensity distribution I in function of the radius r, the beam 4ad having a maximum intensity of $I_{max}$. Such a so called single mode laser beam is often used since it provides largest energy concentration, and for example creates deep holes. The effect of a laser beam shaping device that reshapes the energy intensity distribution of the laser beam 4 is schematically disclosed with a laser beam 4ae having a hard-edged and homogenous intensity distribution of intensity $I_h$. In reality these laser beams 4ad, 4ae are three-dimensional geometrical figures. The volume of these figures have physical sense of energy of the laser beams 4ad, 4ae. E1,E2,E3 and E4 indicate different parts of the figures. These parts could be interpreted as parts of beam energy. E3 is the effective "cylinder" of energy and corresponds to the energy of the reshaped laser beam 4ae. E1 is an apex of Gauss function in an excess of energy over the intensity Ih of the reshaped laser beam 4ae. E1 is a loss of energy and also leads to bad effects regarding the shape of the created micropore. E2 and E4 are the tails of Gauss function that are losses of energy and also lead to bad effects, for example regarding the shape of the created micropore or regarding overheating of tissue. From the point of view of creating precisely shaped pores and/or saving energy to create pores and/or avoiding damages of the biological membrane, only the energy of part E3 is of interest, whereas the energy of parts E1, E2 and E4 are losses. In other word using a laser beam 4ad with a Gaussian intensity distribution when creating pores in a biological membrane has the effect that for example about 40% of the energy is effective to create the part E3, and for example about 60% of the energy is lost due to bad effects. Of course this example is based on the simplified geometrical interpretation based on FIG. 10a, but it clearly shows the effect of losses of laser energy, and it clearly shows the effect of using a beam shaping device that reshapes the energy intensity distribution of the laser beam. A usual laser source has a beam intensity distribution of a Gauss-function. The beam shaping device that reshapes the energy intensity distribution of the laser beam causes a hard-edged intensity distribution, which usually means a steeper slope on the side and/or a flat top, so that the profile shows a distinct edge. Very often a beam homogenizer is used to cerate an about homogeneous distribution, also called a flattop or a top-hat profile, having a shape close to a rectangle, as disclosed in FIG. 2m. This beam shaping can be provided by specially designed optical systems, for example so called homogenizers.

Figure 10B:
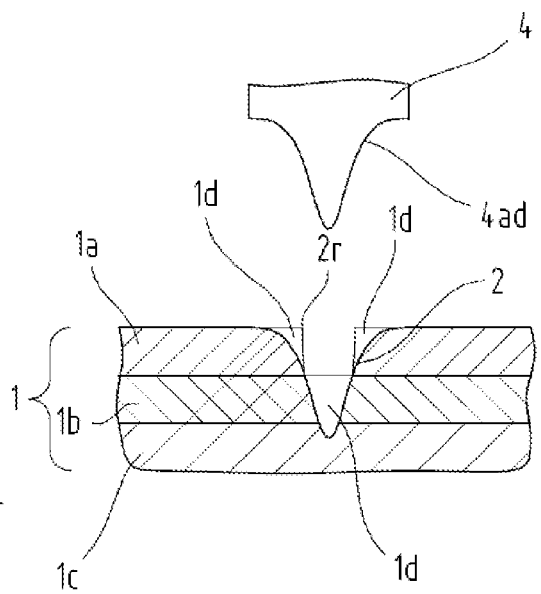
FIG. 10b shows a pore created without beam shaping.
Figure 10C:
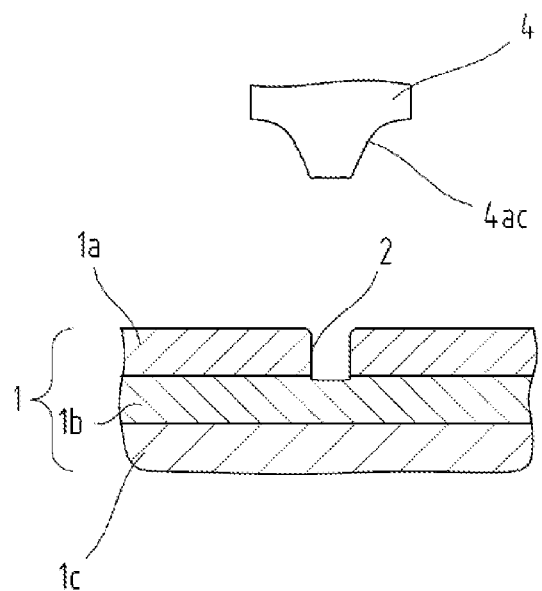
FIG. 10c shows a pore created with beam shaping.
Figure 10D:
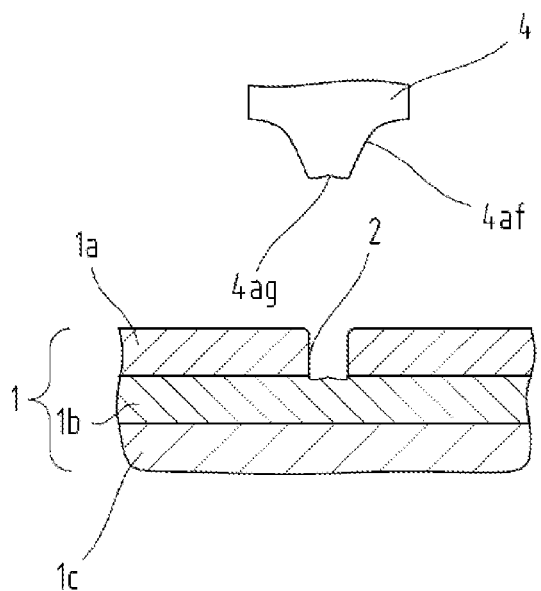
FIG. 10d shows a pore created with beam shaping

FIG. 10b shows a pore 2 in the skin 1 created with a beam 4 without beam shaping, the beam 4 having a Gaussian intensity profile 4ad. FIG. 10c shows a pore 2 in the skin 1 created with a beam 4 using beam shaping, beam 4 having a top hat intensity profile 4ac. The created pore 2 being cylindrical or almost cylindrical. FIG. 10b also shows a dotted line 2r, which corresponds about to the shape of the pore 2 disclosed in FIG. 10c. Compared to the pore 2 created in FIG. 10b, the laser beam 4 applied in FIG. 10b ablates in excess a tissue volume marked with 1d, which also needs additional energy. Therefore, to create a pore 2 as disclosed in FIG. 10c needs less energy than the pore 2 disclosed in FIG. 10b. The pore disclosed in FIG. 10b has for example the further disadvantage that this pore 2 causes pain. FIG. 10d shows a pore 2 in the skin 1 created with a beam 4 using beam shaping, the beam 4 having a top hat intensity profile 4af including a dip 4ag. The dip 4ag shows a decrease in the maximum energy of the beam 4. The dip may have up to 30% less energy than the maximum energy of the beam 4, preferably 10%, 20% or 30% less energy. As disclosed the intensity profile 4af has also a hard-edged intensity distribution.

Most preferably the laser beam 4a has a wavelength between 2.8 and 3.1 microns, and a pulse temporal width between 50 ns and 150 ns. One advantage of such a laser beam 4a is that the effect of energizing or heating of tissue adjacent the created pores 2 is very low, which causes less destruction of cells. Using a conventional laser diode having a wavelength of between 700 and 1200 nm would lead to a highly inefficient formation of pores 2, because lipids would be heated of up to 500° C., which leads to strongly increased damage zones in adjacent tissue. In contrast using a wavelength between 2.8 and 3.1 microns hardly heats lipids. A further advantage is that the measurement of the depth of the pore 2 is easy and precise, because the bottom end of the pore 2 can easily be detected. In contrast the pores 2 disclosed in FIGS. 2r and 2s have no clear bottom end. Therefore it is difficult or even not possible to measure the depth of the pore 2.

FIG. 2u shows a further laser micro-porator 10 comprising a laser source 7 and a laser beam shaping and guiding device 8. The laser source 7 comprises an array of laser diodes 7c, preferably a plurality of linear arranged laser diode emitters, also called laser diode bars which additionally can be stacked together to so called laser diode stacks for more output power. The laser diodes 7c are preferably tempered by a thermo electrical element 7i, to keep the temperature of the laser diodes 7c on an about constant level due to various environment temperatures from 10° C. to 40° C. The emitted wave length of the laser diodes 7c depends on the temperature. The thermo electric element 7i may be used to keep the emitted wave length on a constant value, or to change the emitted wave length by changing the temperature of the diodes 7c. The emitted light of the laser diodes 7c passes through lenses 7i, 7l and a dichroic mirror and hits on the impact point 7q a rotating laser crystal 7n, e.g. an Er:YAG disc. The laser crystal 7n, which has the shape of a disc, is mounted on a laser crystal mount 7t like e.g. copper and connected with a drive 7o with rotating axis 7p. A motor 7o drives the laser crystal mount 7t, so that the laser crystal 7n rotates around the axis 7p. The laser crystal 7n is optically pumped by the beam of the laser diode bar or stack 7c, so that the laser crystal 7n emits a laser beam which is reflected between the dichroic mirror 7m through the Q-switch 7r and the output coupler 7s and which partially passes the output coupler 7s due to it's transmission properties for the laser beam's wavelength of a few percent to the laser beam shaping and guiding device 8. The laser diode 7c may for example have a wavelength of 965 nm, and the laser beam 4 leaving the laser source may for example have a wavelength of about 2.94 micron (μm).

The laser beam 4, coupled out of the laser source 7, may for example have a beam diameter of 1 mm. This exiting beam is widened by lenses 8b, 8a to a preferably parallel beam 4b of for example 4 mm. Following lens 8a, a beam homogenizer 8y and a spherical lens 8x are arranged on a common carrier, driven by a drive 8c, to focus the laser beam 4 onto the surface 1. The beam 4 is deflected by mirrors 8f, which are moved by drives 8g, for example stepper motors, and a control device 11. The area within which the beam 4 can be directed onto the surface 1 may for example have a total diameter of 20 mm. The beam 4 hitting the surface 1 or the micro pore 2 has preferably a diameter of less than 600 μm. A beam splitter 8z may be used, if for example a further laser beam 9d is directed to the surface 1, as disclosed in FIG. 2, or if for example an imaging device is used to get a detailed view of the surface 1 or to analyse the pore geometry or spectrographically analyse fluorescence of tissue or tissue plume. The length of the path of the laser beam 4 between the laser source 7, which means after leaving the source 7 at output coupler 7s, and the surface 1 is preferably within a range of up to 10 cm.

The micro-porator 10 comprises a power supply 10c, such as a battery, rechargeable battery, replaceable battery, fuel cell, photovoltaic cell and so on. The power supply 10c is arranged within the housing 10d of the micro-porator 10.

FIG. 2x shows an example of a laser beam shaping device 8y, a beam homogenizer 8y in more details. The beam homogenizer 8y consists of two microlens arrays with identical lens pitch. Square-type lens apertures are used to generate, out of the laser beam 4b, a square flat top intensity distribution in the Fourier plane FP, which is also a focal point FP. The spherical lens 8x focuses the beam 4 onto the focal point FP, where the beam has the shape of a square. The beam 4 for example has a depth of focus of about 1 mm at the focal point FP.

Figure 2V:
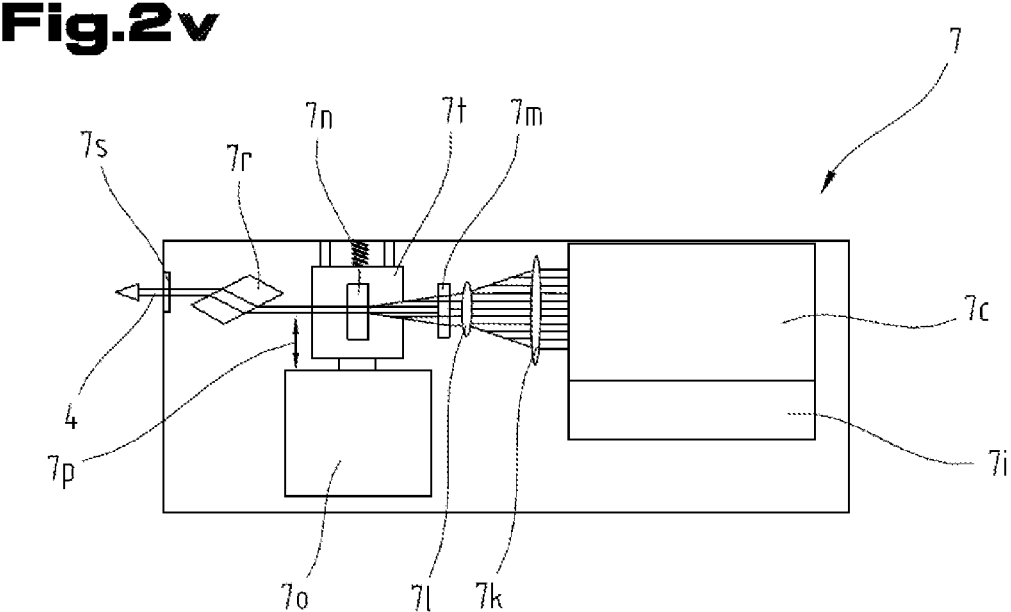
FIG. 2v, 2w show two laser sources.

In contrast to the laser source 7 disclosed in FIG. 2u, where the laser crystal 7n rotates, the laser source 7 of FIG. 2v uses a linear slab 7n, preferably an Er:YAG crystal, which is held in an e.g. aluminium mount 7t, and which is moved in linear direction 7p by a drive 7o.

Both laser sources 7 disclosed in FIGS. 2u and 2v are preferably operated with nanosecond pulses delivered at rates between 200 Hz and up to 20 kHz. The moving laser crystal 7n allows to overcome the problem of the terminal level lifetime of the crystal 7n, which usually limits the maximal repetition rate. By permanently moving or positioning the laser crystal 7n during operation of the laser source 7, successive pulses emitted by the laser LED 7c do not impact the same area on the crystal 7n, and therefore the terminal level lifetime of the laser crystal 7n doesn't affect the maximal repetition rate, with which the crystal 7n may emit a laser pulse any more. This allows creating a high frequency output laser beam 4, for example in the range up to 20 kHz, and with a wavelength of for example 2.94 μm, and with a pumping wavelength of for example 965 nm.

Figure 2W:
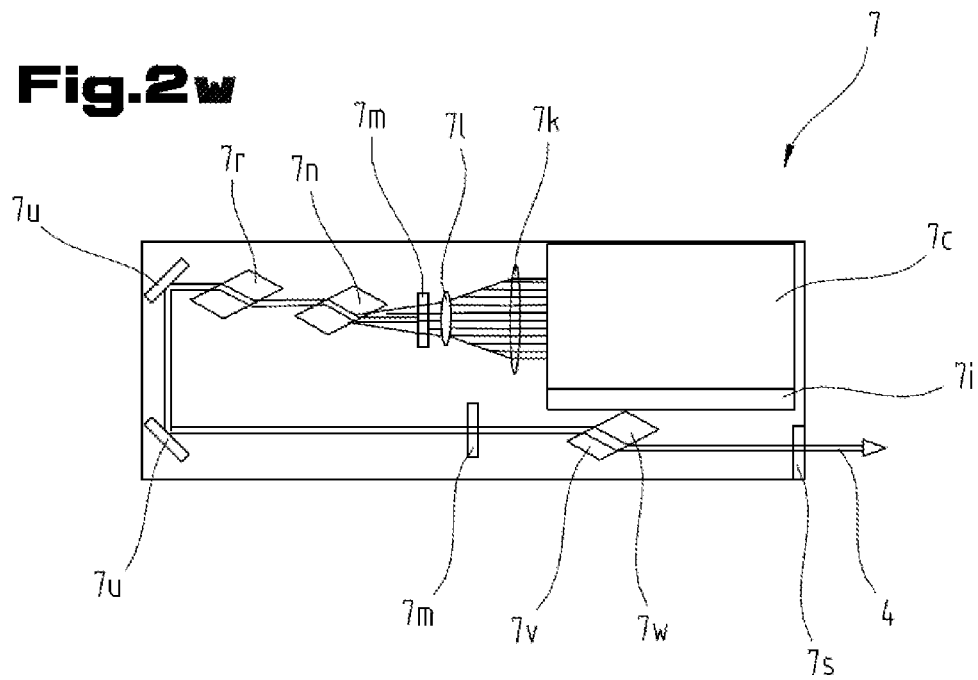

FIG. 2w shows a further laser source 7, comprising a laser diode bar or stack 7c pumping e.g. a Nd doped laser crystal 7n with nanosecond pulses. Along the path of beam 4, lenses 7k, 7l, a dichroic mirror 7m, a laser crystal 7n, a Q-switch 7r, two or more high reflection mirrors 7u for beam folding, a further dichroic mirror 7m, a nonlinear optical (NLO) crystal 7v and an output coupler 7s are arranged. The NLO crystal 7v may be turned around an axis 7w. The NLO crystal singly resonant optical parametric oscillator (OPO) 7v is pumped by the, Q-switched e.g. Nd doped laser. Turing the NLO crystal 7v around the axis 7w results in a tunable (for example 2.6-3.2 μm) OPO idler output, whereby preferably 2.95 μm is used.

Figure 4A:
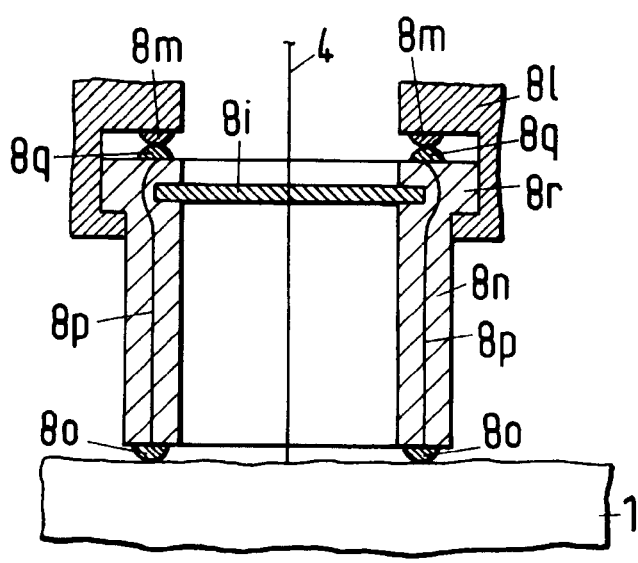
FIG. 4a shows a cross section of a tip suitable for a micro-porator.

FIG. 4a shows a disposable tip 8n that is optionally fitted into the laser housing 8l of the laser-porator 10 and is positioned proximal to the ablation site. The tip 8n forms a container with a cylindrical wall and a protective glass 8i. This container collects the ablated tissue and other matter released by the ablation. The tip 8n can be shaped so as to allow easy insertion into the laser-porator 10. The protective glass 8i is an at least partially transparent medium for the laser beam 4 and may be made of glass, polycarbonate or another medium that is at least partial transparent for the laser beam 4. The tip 8n disclosed comprises electrical contact elements 8o, 8q that are connected by an electrical wire 8p. The contact elements 8q are connected with the contact elements 8m of the laser housing 8l. This arrangement allows measuring the impedance of the skin 1 between the contact elements 8o. The tip can further comprise an adhesive strip, which is optionally thermo sensitive.

Figure 4B:
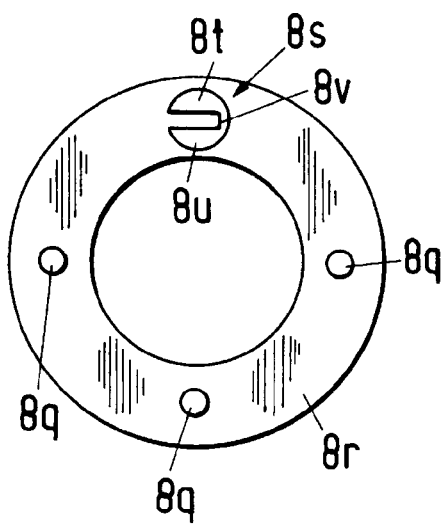
FIG. 4b shows a front surface of the tip.
Figure 4C:
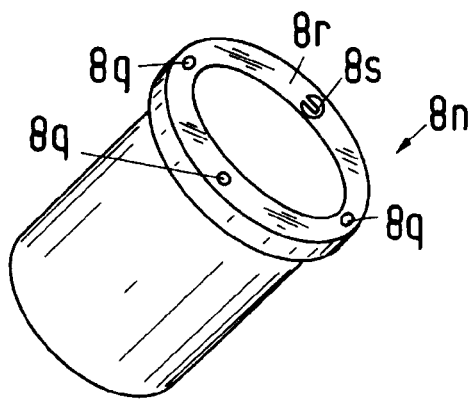
FIG. 4c shows a perspective view of the tip.
Figure 4D:
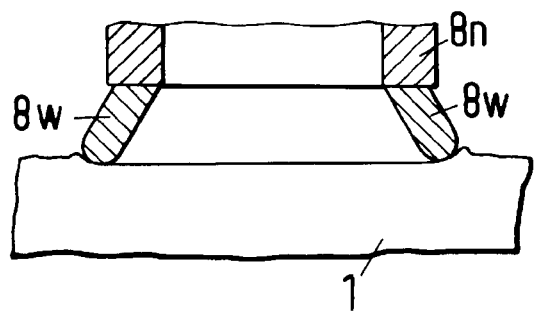
FIG. 4d shows the front end of a further tip.

This arrangement is preferably used as an interlock mechanism, to make sure that the tip 8n is arranged onto the skin, before the laser source 7 is activated. The tip 8n can comprise also sensors, for example sensors to measure humidity, temperature or pH-value of the skin. Also these sensors can be used as an interlock mechanism. Because in a preferred embodiment a parallel or quasi-parallel laser beam is used, which might cause injuries if not handled properly, it is of utmost importance that the laser beam 4 is only activated when the tip 8n is placed onto the skin. As shown in FIGS. 4b and 4c the disposable tip 8n can comprise a safety mechanism 8s which allow using the tip 8n only once. The safety mechanism 8s comprises two contact elements 8t, 8u, with mating contacts in the laser housing 8*l*, and a fusing element 8*v* that evaporates after a current has been applied, or breaks mechanically or is an electronic device, e.g. a microchip, which can be reprogrammed. After the poration is finished such a change is applied onto the safety mechanism 8*s*. The status of the safety mechanism 8*s* is controlled by the laser porator 10 so that the tip 8*n* can only be used once. The tip 8*n* can comprise means 8*w* to stretch the skin 1 in front of the tip 8, for example, an elastic ring as disclosed in FIG. 4*d*. When the tip 8*n* is pressed onto the skin 1, this elastic ring pushed the skin 1 outward in radial direction, so that the skin within the elastic ring is stretched and the surface of the skin is mainly plain.

Figure 5A:
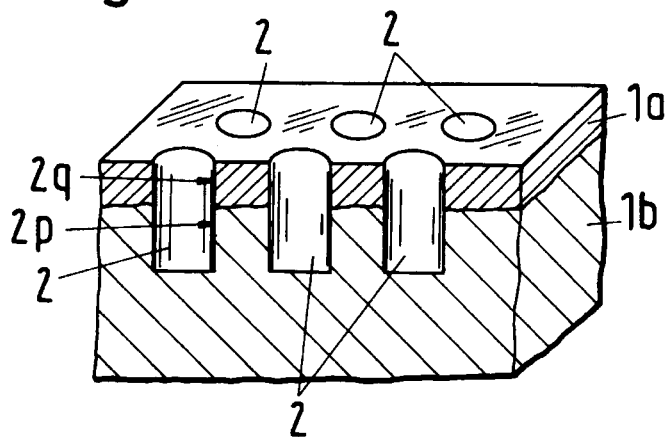
FIG. 5a-5c are perspective view of examples of suitable shapes of micro-porations.

FIG. 5*a* shows an array of individual pores 2 in the skin 1. All individual pores 2 have about the same shape and depth.

Figure 5B:
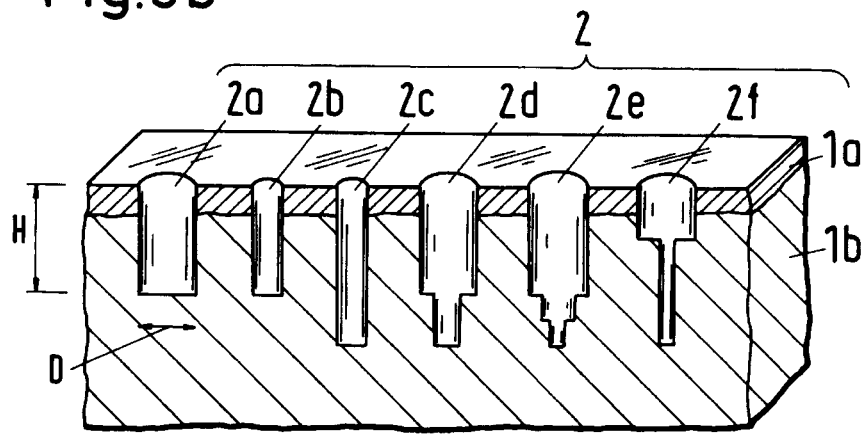
Figure 5C:
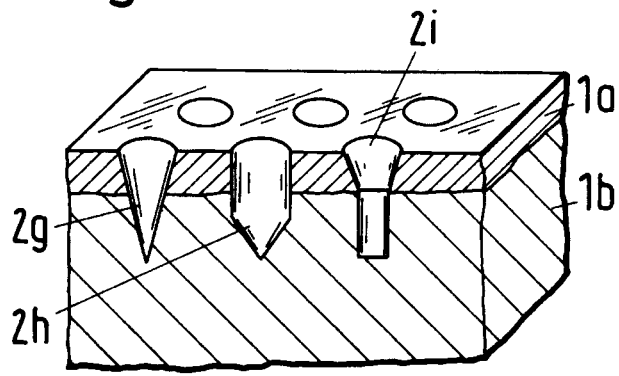

FIG. 5*b* shows individual pores 2*a* to 2*f* of various shapes, which can be created with support of the poration controller 11 controlling the laser porator 10. To produce the individual pores shown in FIG. 5*b*, at least the cross-section of the laser beam 4 has to be varied. In a preferred embodiment, the laser porator 10 varies the cross-section and/or the energy density of each consecutive pulsed laser beam 4, which allows creation of individual pores 2 with numerous different shapes. If the ablated layer per laser beam pulse 4 is very small, even conically shaped individual pores 2*g*,2*h*,2*i*, as disclosed in FIG. 5*c*, can be created.

Figure 5D:
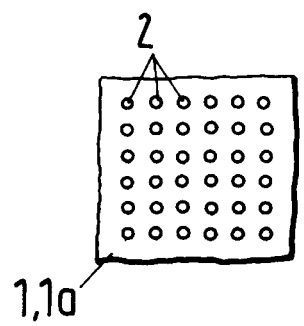
FIG. 5d, 5f shows a plan view of the skin with an array of micro-porations.

FIG. 5*d* shows a plan view of the skin having a regular array of individual pores 2 that collectively form a micro-poration. The micro-poration on the biological membrane, after the laser porator 10 has finished porating, is called "initial microporation". The poration memory 12 contains the initial microporation dataset, which define the initial microporation. The initial microporation dataset comprises any suitable parameters, including: width, depth and shape of each pore, total number of individual pores 2, geometrical arrangement of the pores 2 on the biological membrane, minimal distance between the pores 2, and so forth. The laser porator 10 creates the pores 2 as defined by the initial microporation dataset. This also allows arranging the individual pores 2 in various shapes on the skin 1, as for example disclosed with FIG. 5*f*.

Figure 5E:
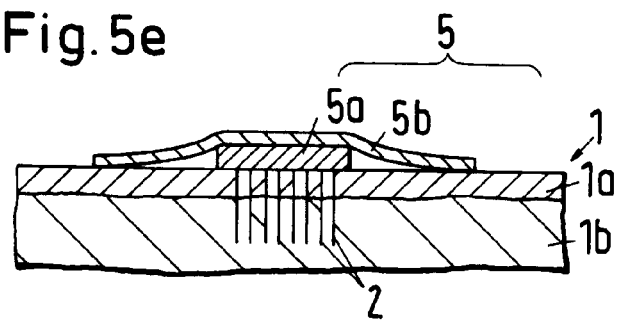
FIG. 5e shows a schematic cross-section of a porated skin with a drug container attached to the skin surface.
Figure 5F:
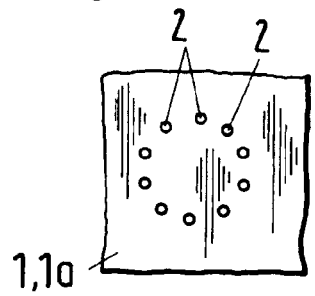

FIG. 5*e* discloses a transdermal patch 5 comprising a drug container 5*a* and an attachment 5*b*, which is attached onto the skin 1, the drug container 5*a* being positioned above an area comprising individual pores 2. The area can have a surface, depending on the number and spacing of the individual pores 2, in the range between 1 mm$^2$ and 1600 mm$^2$, Preferred 20×20 mm, e.g. a surface of 400 mm$^2$.

For each individual pore 2*i*, the surface of the inner wall and the surface of the lower end are of importance, in particular the permeation surface Ai, being the sum of both of these surfaces. In a preferred embodiment, the laser porator 10 comprises the distance measurement apparatus 9, which facilitates determining the permeation surface Ai very accurately. In a further preferred embodiment, the beginning of the epidermis is estimated by first determining the thickness of the stratum corneum. This in turn permits determination of a corrected permeation surface Ai for each individual pore 2*i*, which establishes the effective permeation surface of the epidermis 1*b*, or which permits to increase the depth of the individual pore 2*i* by the thickness of the stratum corneum. This permeation surface Ai can easily be calculated for each individual pore 2*i*. If the individual pore 2*i* has the shape of, for example, a cylinder, the permeation surface Ai corresponds to the sum of $D*\pi*H$ and $(D/2)^2*\pi$, D being the diameter of the individual pore 2, and H being the total depth of the individual pore 2 or the depth of the individual pore 2 within the epidermis 1*b*. The effective permeation surface Ai in the pore 2 often doesn't correspond exactly to the geometrical shape, defined by D and H because the surface of the pore 2 may be rough or may comprise artefacts, which means the effective permeation surface is bigger than the calculated permeation surface Ai. The permeation surface Ai is at least a reasonable estimate of the effective permeation surface. Usually there is only a small or no difference between the permeation surface Ai and the effective permeation surface in the pore 2. The total permeation surface A of n individual pores 2*i* is then the sum A of all permeation surfaces Ai of all individual pores 2*i*.

Each individual pore 2 of the epidermis has a cell growth of usually 10 to 15 µm per day, the cells growing from the lower end of the individual pore 2 in direction Z to the stratum corneum 1*a*. This cell growth causes the permeation surface Ai of each individual pore 2*i*, respectively the total permeation surface A of all individual pores 2 to decrease in function of time. Depending on the total number of individual pores 2, which can be in a range of up to 100 or 1000 or 10000 or even more, the geometrical shape of the individual pores 2, and taking into account the effect of cell growth, the total permeation surface in function of time can be varied in a wide range. The total permeation surface in function of time can be predicted and calculated by an appropriate choice of the number of pores 2 and their geometrical shape and optional added regeneration delayer (occlusive bandage, diverse chemical substances, etc.).

Figure 6A:
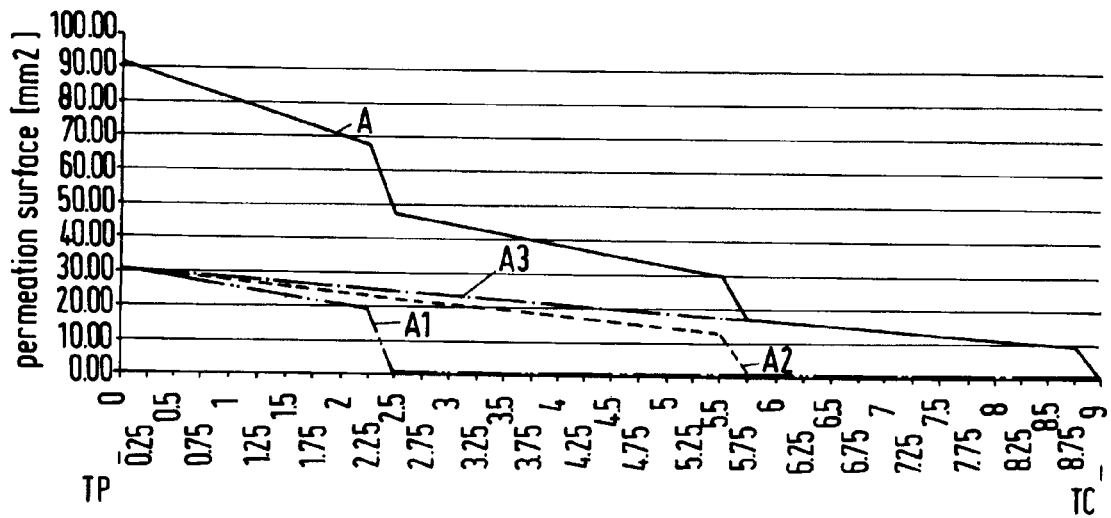
FIG. 6a-6b shows the permeation surface of all micropores over time.
Figure 6B:
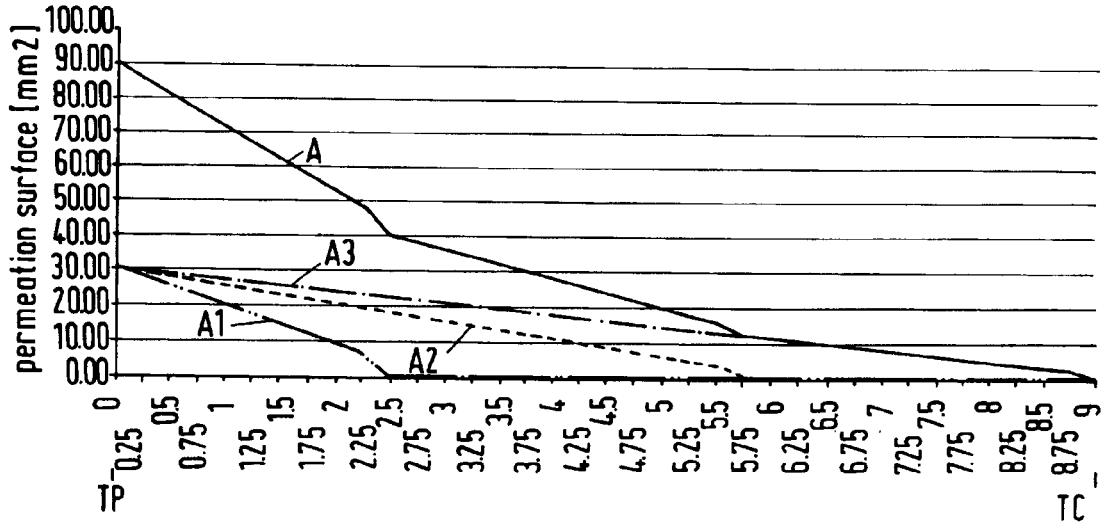

FIGS. 6*a* and 6*b* show examples of the total permeation surface A as a function of time. FIGS. 4*a* and 4*b* show the corrected total permeation surface A(t), which is the total permeation surface A(t) of the epidermis 1*a* only. The laser-porator 10 allows to micro-porating a biological membrane 1 by the creation of an array of micropores 2 in said biological membrane 1, whereby the number of micropores 2 and the shape of these micropores 2 is properly selected so that the sum of the micropores 2 forming an initial permeation surface, and that the permeation surface A (t) of the initial permeation surface decreases in a predetermined function over time, due to cell growth in the micropores 2.

The initial microporation dataset according to FIG. 6*a* comprises three groups of cylindrical micropores 2 with different shapes:
- a first group consisting of 415 pores with a diameter of 250 µm, a depth of 50 µm and a permeation surface A1 as a function of time.
- a second group consisting of 270 pores with a diameter of 250 µm, a depth of 100 µm and a permeation surface A2 as a function of time.
- a third group consisting of 200 pores with a diameter of 250 µm, a depth of 150 µm and a permeation surface A3 as a function of time.

The total permeation surface A as a function of time is the sum of all three permeation surfaces A1, A2 and A3.

All individual pores 2*i*, which means the initial microporation, is created within a very short period of time, for example, within a time range of a fraction to a few seconds, so that beginning with the time of poration TP, the sum of all created pores 2*i* forming an initial permeation surface, which, due to cell growth, decreases as a function of time. At the time TC all individual pores 2*i* are closed, which means that the barrier properties significantly increase.

The initial microporation dataset according to FIG. 6*b* consists also in three groups of cylindrical micropores 2 with different shapes:
- a first group consisting of 4500 pores with a diameter of 50 µm, a depth of 50 µm and a permeation surface A1 as a function of time.

a second group consisting of 2060 pores with a diameter of 50 μm, a depth of 100 μm and a permeation surface A2 as a function of time.

a third group consisting of 1340 pores with a diameter of 50 μm, a depth of 150 μm and a permeation surface A3 as a function of time.

The total permeation surface A is the sum of all three permeation surfaces A1, A2 and A3.

Depending on the number of pores 2 and their shape, in particular the diameter and depth of the pores 2, the function over time of the total permeation surface A can be varied in a wide range. This makes it clear that the poration of individual pores 2 does not only determine the initial permeation surface, but also the function of the total permeation surface A over time. FIGS. 6a and 6b show the total permeation surface A over a time period of 9 days, starting with an initial permeation surface of 90 mm². The permeation surface A decreases within 9 days to a very small value or to zero. Depending on the shape of the individual pores 2, the time period may be much shorter, for example, just 1 day, or even shorter, for example, a few hours.

Figure 7:
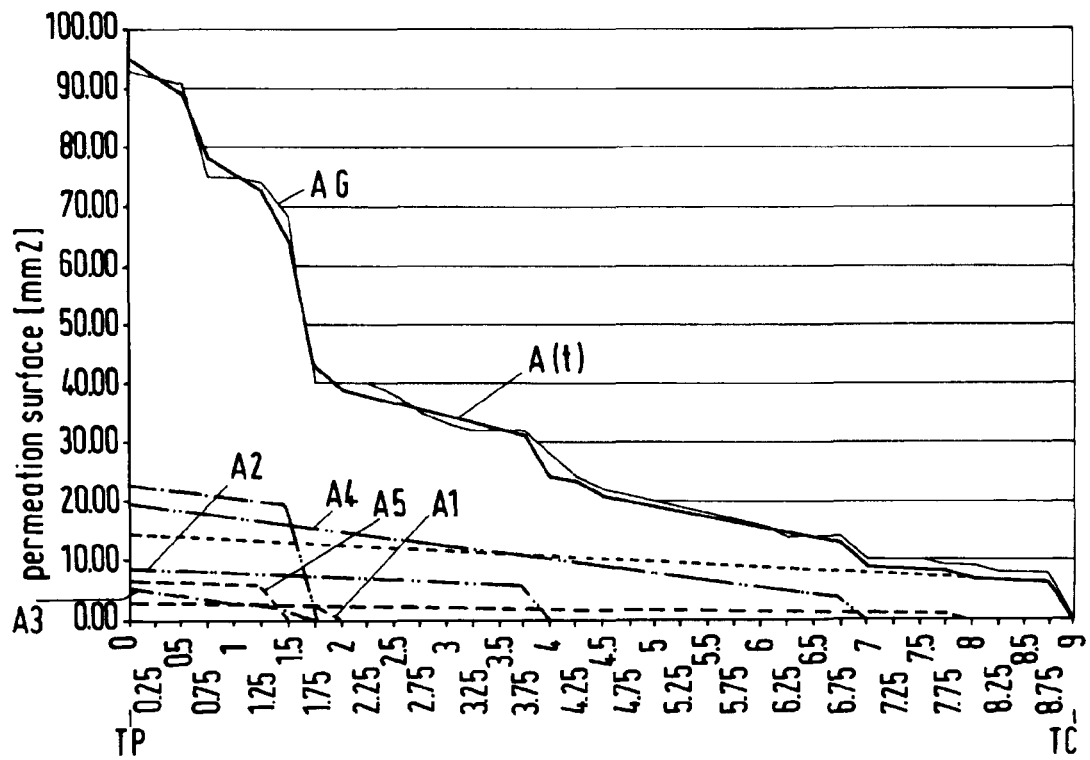
FIG. 7 shows the a given permeation surface and a created permeation surface.

Almost any permeation surface A(t) as a function of time may be establish by a proper selection of the number and the shape of the individual pores 2. FIG. 7 shows a given function AG of a permeation surface as a function of time. FIG. 7 also shows the permeation surface of different groups A1, A2, A3, A4, A5, . . . of individual pores 2 over time. Each group being defined by the number of pores, the diameter and the depth. All individual pores 2 have cylindrical shape. By combining the individual permeation surfaces (A1, A2, A3, A4, A5, . . . ) of all the groups, a permeation surface A(t) is achieved, which function is quite similar to the given function AG. The different groups of individual pores, their number and their shape can be determined by mathematical methods known to those skilled in the art.

Figure 8:
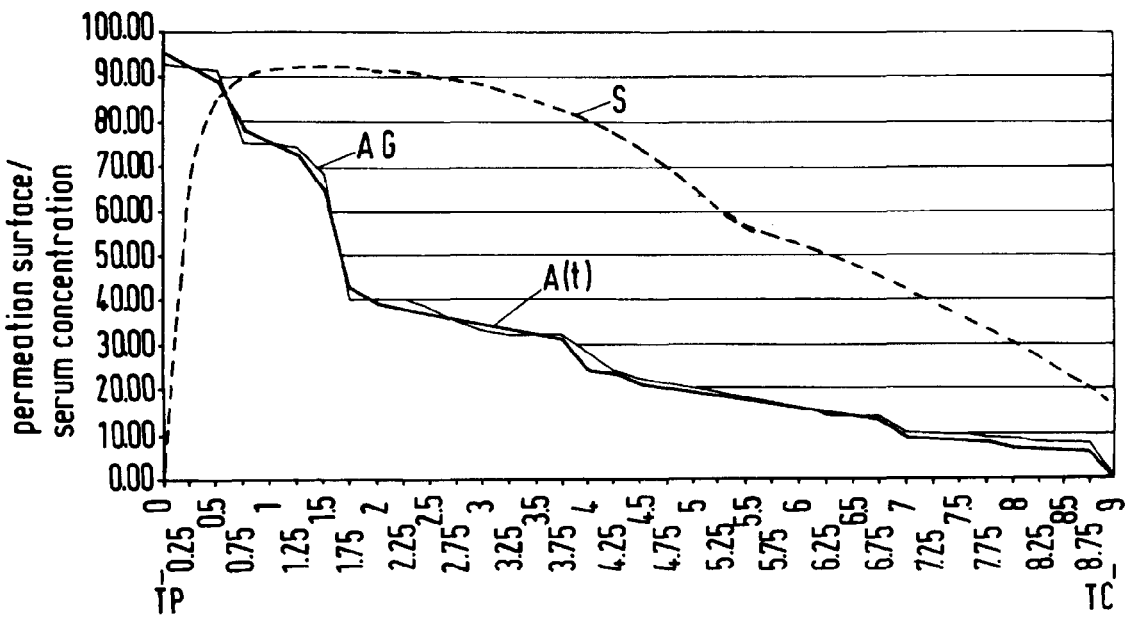
FIG. 8 shows transdermal delivery of a drug over time, in combination with a permeation surface.

FIG. 5e shows a patch 5 containing a drug 5a and being fixed onto the skin 1, above the individual pores 2. FIG. 8 shows the serum concentration S of this drug as a function of time in the blood. The drug is entering the permeation surface by passive diffusion. The amount of drug entering the permeation surface is mainly determined by the permeation surface A(t) over time. Therefore, the serum concentration as a function of time can be determined by an appropriate poration of the skin 1 with an initial microporation at time TP.

Figure 9A:
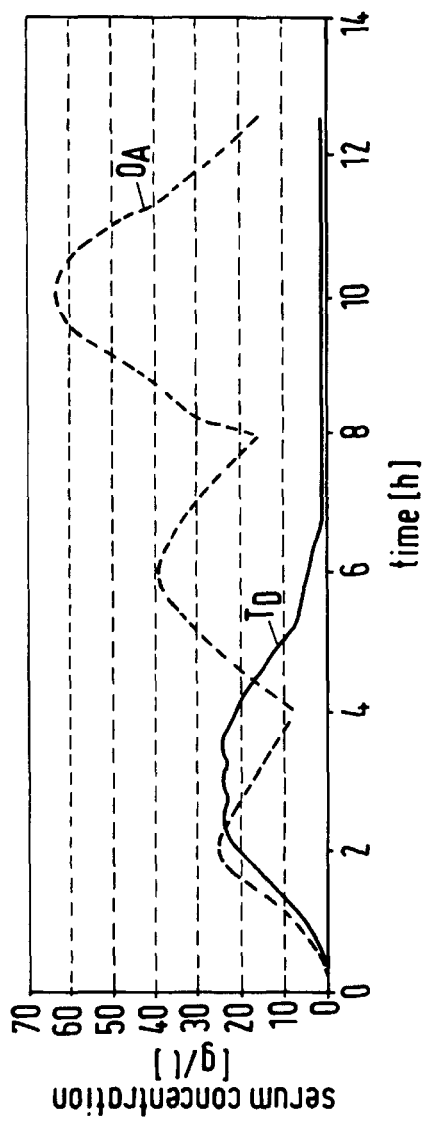
FIG. 9a-9b show the serum concentration of a drug over time, with the same amount of drug but different permeation surfaces.
Figure 9B:
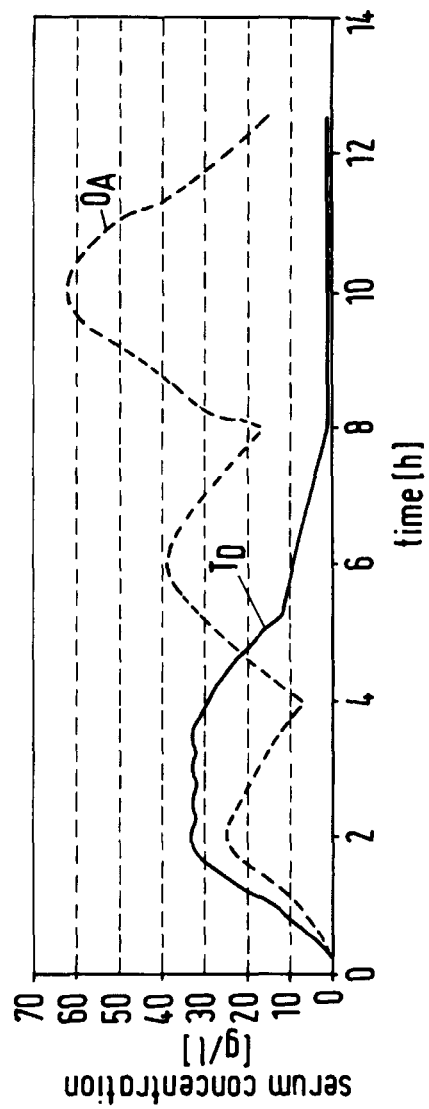

FIG. 9a to 9b show the administration of the same amount of drug, for example 100 mg acetylsalicylic acid, the drug being arranged on the skin 1 as disclosed in FIG. 5e. Depending on the permeation surface A(t) as a function of time, the level of the serum concentration as well as the time period within which the drug is released, can be predescribed. In FIG. 9a the permeation surface A(t) is chosen such that the maximal serum concentration is about 25 g/l over a short period of time of about two hours. FIG. 9b shows a fast application (turbo) of the drug, with maximal serum concentration of about 30 g/l over a short period of time of about two hours. One advantage of the invention is, that with transdermal application TD the serum concentration reaches an about constant value, in contrast to oral application OA, which shows a heavy fluctuation. A further advantage is that the same amount of drug, e.g. the same patch, applied onto the skin 1, causes a different serum concentration, depending only on the function of the permeation surface A over time. This allows administering the same drug in different ways. This also allows administering the same drug in an individual way, in that the permeation surface is created depending on individual parameters of the person the drug is applied to.

This also allows using the micro-porator to treat diseases. The method of treating a disease comprises: applying repeated beams of energy to each of a plurality of spots in the skin of a patient for the purpose of producing pores having a desired dimensional characteristic for transdermal delivery of a drug contemplated to induce a desired effect; and applying the drug to the pores such that the drug is absorbed into the skin through the pores in an amount effective to induce the desired effect. The desired effect is usually to treat or cure the disease. The beam of energy comprises a laser, but can instead also comprise a beam to create plasma. The dimensional characteristic usually comprises a pore depth, the pore depth being between 5 μm and 200 μm. The method further comprises producing at least ten of the pores in the patient, each of which is at least 1 μm across and at least 1 μm in depth. The method further comprises providing feedback between an earlier pulse and a later pulse with respect to the dimensional characteristic, and automatically altering the later pulse as a function of the feedback. The step of applying the drug to the pores preferably comprises applying the drug to the skin with a patch.

The method of marketing a laser apparatus comprises providing instruction to a medical professional to apply repeated beams of energy to each of a plurality of spots in the skin of a patient for the purpose of producing pores having a desired dimensional characteristic for transdermal delivery of a drug contemplated to induce a desired effect. The desired effect is usually to treat or cure the disease. The method preferably further comprises advising the professional to apply the drug to the pores such that the drug is absorbed into the skin through the pores in an amount effective to induce the desired effect. The dimensional characteristic preferably comprises a pore depth, and further comprising advising the professional that a suitable pore depth is between 5 μm and 200 μm. The instruction preferably further comprises advising the professional that the apparatus provides feedback between an earlier pulse and a later pulse with respect to the dimensional characteristic, and automatically alters the later pulse as a function of the feedback.

The micro-porator 10 can also be used for pure cosmetic treatment in that the biological membrane 1, for example the skin, is porated so that it has a plurality of individual pores 2. These pores 2 initiate a cell growth in the epidermis so that these pores 2, after a certain time, become filled with newly generated cells. The only object is to beautify the human or animal skin for cosmetic reasons. This cosmetic treatment, creating an array of micropores, can be repeated several times, for example every ten days, to cause a cell growth in a lot of areas.

The feedback loop 13, the respective apparatus 9 to measure the depth of an individual pore 2 as well as the poration controller 11 may be used with any kind of micro porator 10, not only with a micro porator 10 utilizing a laser beam as disclosed with the present invention, but also with a micro porator 10 utilizing mechanical, hydraulic, sonic, electromagnetic, electric or thermal means to perforate wholly or partially a biological membrane such as the skin or mucosal layers of a human being or a mammal, or the outer tissue layers of a plant.

The invention claimed is:

1. A laser micro-porator (10) for porating a biological tissue (1), comprising:
   a) a solid state laser source (7) that is configured to emit a pulsed beam (4);
   b) optics (8a,8b,8x) configured to modify the pulsed beam such as to direct a first laser beam (4) of less than 1 mm width on the biological tissue (1), wherein the biological tissue comprises stratum corneum, epidermis, and dermis;

c) a deflector (8f) configured to controllably direct the first laser beam (4) in various directions, one direction at a time;

d) a laser beam shaping device that is configured to reshape the energy intensity distribution within the first laser beam (4);

e) a poration controller (11) that is configured to control the laser source (7) and the deflector (8f) to create a poration comprising a plurality of individual pores (2) in the biological tissue (1), wherein the individual pores extend through the stratum corneum and part of the epidermis but not into the dermis, wherein the poration controller (11) is configured to control the laser source (7) to emit pulses of the first laser beam (4), and further configured to direct the pulses to impact a single one of the plurality of pores (2) at least twice;

f) a feedback mechanism (13) that is operationally coupled to the poration controller, and configured to analyze a characteristic of the single one of the plurality of pores (2); and g) wherein the poration controller (11) is further configured to compare the characteristic of the single one of the plurality of pores with a preset value, and to prevent a further pulse of the first laser beam from being directed into the single one of the plurality of pores if the characteristic of the single one of the plurality of pores is at least as great as the preset value.

2. The laser porator of claim 1, wherein the laser beam shaping device is configured to reshape the energy intensity distribution within the laser beam (4) to form a hard-edged intensity distribution.

3. The laser porator of claim 2, wherein the beam shaping device comprises a beam homogenizer (8y, 7h) configured to form a homogenous intensity distribution of the first laser beam (4).

4. The laser porator of claim 3, wherein the optics (8a, 8b, 8x) is configured to focus the first laser beam (4) on the biological tissue (1), and wherein the first laser beam (4) has a homogenous intensity distribution at the focus.

5. The laser porator of claim 3, wherein the intensity distribution of the first laser beam (4) has a shape of a top hat profile.

6. The laser porator of claim 3, wherein the homogenous intensity distribution of the first laser beam (4) varies less than 10%.

7. The laser porator of claim 2, wherein the beam shaping device is configured to reshape the beam (4) to have a dip in the centre of the intensity distribution.

8. The laser porator of claim 1 wherein the pulsed beam (4) has a wavelength in the range of 2 microns to 10 microns.

9. The laser porator of claim 8, wherein the pulsed beam (4) has a wavelength between 2.8 microns and 3.1 microns.

10. The laser porator of claim 1, wherein the pulsed beam (4) has a wavelength of less than 200 nanometers.

11. The laser porator of claim 1 wherein the pulses have a temporal width between 1 ns and 1 μs.

12. The laser porator of claim 11, wherein the pulses have a temporal width between 10 ns and 150 ns.

13. The laser porator of claim 1 wherein a pulse repetition frequency of the laser source (7) is higher than 200 Hz.

14. The laser porator of claim 1 wherein the laser source (7) comprises a Q-switch (7f) and a laser crystal (7b) pumped by a laser diode (7c).

15. The laser porator of claim 1 wherein the laser porator is configured to allow porating the biological tissue (1) without active cooling.

16. The laser porator of claim 15, wherein at least one of the porator and the controller are configured to porate the biological tissue (1) in less than 10 seconds.

17. The laser porator of claim 1 wherein the laser source (7), the optics (8a,8b), the deflector (8f), the laser beam shaping device (7h, 8y) and the poration controller (11) are at least partially enclosed within a housing sized and shaped to fit in a hand of a laser porator user.

18. The laser porator of claim 17, further comprising an autonomous power supply (10c) within the housing that is configured to power the laser porator.

19. The laser porator of claim 1 wherein the optics (8a, 8b) is configured to produce a parallel or quasi-parallel laser beam (4) on the biological tissue (1).

20. The laser porator of claim 1, wherein the feedback mechanism (13) is further configured to analyze the characteristic of the single one of the plurality of pores (2) each time the laser beam (4) has been emitted to the single one of the plurality of pores.

21. The laser porator of claim 20, wherein the analysis is based on reflected light.

22. The laser porator of claim 20, wherein the feedback mechanism (13) comprises a spectrograph (13) that is configured to spectrographically evaluate the single one of the plurality of pores (2).

23. The laser porator of claim 20, wherein the feedback mechanism (13) is configured to measure the depth of the single one of the plurality of pores (2).

24. The laser porator of claim 23, wherein the feedback mechanism (13) includes a second laser beam (9d) having a width of less than the first laser beam (4).

25. The laser porator of claim 24, wherein the feedback mechanism (13) includes a device (9e) that is configured to deflect the second laser beam (9d) into the single one of the plurality of pores (2) and onto a reference site (X) on the surface of the biological tissue (1).

26. The laser porator of claim 20, wherein the controller (11) is further configured to compare a characteristic of the individual one of the plurality of pores (2) with a preset range, and to prevent a further pulse of the first laser beam (4) from being directed into the individual pore (2) if the characteristic of the individual pore (2) is within a preset range.

27. The laser porator of claim 1, wherein the preset value is a depth of the pore (2) having a value between 5 μm and 200 μm.

28. The laser porator of claim 1 further comprising optics (8a,8b,8x) that is configured to shape the first laser beam (4) to have a width between 0.05 and 0.5 mm.

29. The laser porator of claim 1 wherein the first laser beam (4) has an energy density of between 100 mJ/cm$^2$ and 5 J/cm$^2$.

30. The laser porator of claim 1 further comprising optics (8a,8b,8x) that is configured to modulate a width of the first laser beam (4).

31. The laser porator of claim 1, further comprising an absorber (8d), and wherein the absorber (8d) is positioned along the path of the beam (4) and wherein the absorber is configured to modulate energy density of the first laser beam (4).

32. The laser porator of claim 1 further comprising a poration memory (12) that is programmed to store parameters for at least one of the plurality of pores (2), including at least one parameter selected from the group consisting of cross-section, depth, shape and permeation surface, and wherein the poration controller (11) further includes at least one of the feedback mechanism (13), optics (8*a*, 8*b*,8*x*), beam shaping device (8*y*) and an absorber (8*d*) that is configured to shape the individual pore (2) according to the parameters of the poration memory (11).

33. The laser porator of claim 32, wherein the poration memory (12) is further programmed to comprise a parameter selected from the group consisting of total number of individual pores (2), geometrical arrangement of the pores (2) on the biological membrane, minimal distance between the pores (2), and total permeation surface of all individual pores (2).

* * * * *